US007785535B2

(12) United States Patent

Chen et al.

(10) Patent No.: US 7,785,535 B2
(45) Date of Patent: Aug. 31, 2010

(54) SAMPLE MULTIPROCESSING

(75) Inventors: Shuqi Chen, Framingham, MA (US); Bertrand Lemieux, Brighton, MA (US); Lingjun Chen, Framingham, MA (US)

(73) Assignee: IQuum, Inc., Marlborough, MA (US)

( * ) Notice: Subject to any disclaimer, the term of this patent is extended or adjusted under 35 U.S.C. 154(b) by 462 days.

(21) Appl. No.: 11/570,184

(22) PCT Filed: Jun. 7, 2005

(86) PCT No.: PCT/US2005/020095

§ 371 (c)(1), (2), (4) Date: Jun. 29, 2007

(87) PCT Pub. No.: WO2005/121963

PCT Pub. Date: Dec. 22, 2005

(65) Prior Publication Data

US 2007/0292858 A1 Dec. 20, 2007

Related U.S. Application Data

(60) Provisional application No. 60/577,692, filed on Jun. 7, 2004.

(51) Int. Cl.
*G01N 21/00* (2006.01)
*G01N 31/00* (2006.01)
*G01N 33/00* (2006.01)

(52) U.S. Cl. ............................ 422/82; 422/55; 422/58; 422/81; 422/68.1; 435/7.1; 435/287.1; 435/287.2; 435/287.6; 435/288.3; 435/288.4; 435/288.7; 435/288.5

(58) Field of Classification Search .................. 422/55, 422/58, 81, 68.1, 82; 435/7.1, 287.1, 287.2, 435/287.6, 288.3, 288.4, 288.7, 288.5
See application file for complete search history.

(56) References Cited

U.S. PATENT DOCUMENTS 3,736,933 A 6/1973 Szabo (Continued)

FOREIGN PATENT DOCUMENTS

WO WO-9900655 1/1999

(Continued)

*Primary Examiner*—Melanie Yu
(74) *Attorney, Agent, or Firm*—Scott E. Kamholz; Foley Hoag LLP

(57) ABSTRACT

A sample processing cartridge may include a plurality of segments arranged in an array at least two rows long and two columns wide. Each segment may be defined by at least one wall of the sample cartridge, fluidly isolated from adjacent segments at least in part by at least one breakable seal or by at least one permanent seal, so expandable as to receive a volume of fluid expelled from another segment, and so compressible as to contain substantially no fluid when so compressed. At least two adjacent segments of at least one row of the array may be aligned along a longitudinal axis of the row and have substantially the same height along a latitudinal axis of the row. At least two adjacent segments in at least one row may be separated by a permanent seal to form at least two tracks. At least one segment, or at least two adjacent segments separated by a breakable seal, may be in fluid communication with the at least two tracks. At least one segment may contain at least one reagent.

15 Claims, 6 Drawing Sheets

U.S. PATENT DOCUMENTS

| | | | | |
|---|---|---|---|---|
| 4,869,286 | A | 9/1989 | Williams et al. | |
| 5,652,149 | A | 7/1997 | Mileaf et al. | |
| 6,068,751 | A * | 5/2000 | Neukermans | 204/601 |
| 6,251,660 | B1 | 6/2001 | Muir et al. | |
| 6,300,138 | B1 | 10/2001 | Gleason et al. | |
| 6,303,389 | B1 | 10/2001 | Levin et al. | |
| 6,318,191 | B1 | 11/2001 | Chen et al. | |
| 6,413,784 | B1 | 7/2002 | Lundsgaard et al. | |
| 6,432,694 | B1 | 8/2002 | Malmqvist et al. | |
| 6,548,263 | B1 | 4/2003 | Kapur et al. | |
| 6,645,758 | B1 | 11/2003 | Schnipelsky et al. | |
| 6,716,629 | B2 | 4/2004 | Hess et al. | |
| 6,748,332 | B2 | 6/2004 | Chen et al. | |
| 6,780,617 | B2 | 8/2004 | Chen et al. | |
| 6,814,935 | B2 | 11/2004 | Harms et al. | |
| 6,964,862 | B2 | 11/2005 | Chen et al. | |
| 7,125,711 | B2 * | 10/2006 | Pugia et al. | 435/288.5 |
| 7,198,759 | B2 * | 4/2007 | Bryning et al. | 422/100 |
| 2002/0151040 | A1 | 10/2002 | O'Keefe et al. | |
| 2003/0049833 | A1 | 3/2003 | Chen et al. | |
| 2004/0105782 | A1 | 6/2004 | Chen et al. | |
| 2004/0161788 | A1 | 8/2004 | Chen et al. | |
| 2004/0223878 | A1 | 11/2004 | Chen et al. | |
| 2006/0154341 | A1 | 7/2006 | Chen et al. | |

FOREIGN PATENT DOCUMENTS

| | | |
|---|---|---|
| WO | WO-0013014 | 3/2000 |
| WO | WO 00/23803 | 4/2000 |
| WO | WO 01/07892 | 2/2001 |

* cited by examiner

| Row | | | |
|---|---|---|---|
| 1 | Germination solution | | |
| 2 | inlet | Filter | outlet |
| 3 | Wash solution | Toxin | Bacteria/Virus |
| 4 | | Magnetic Ab bead capture | |
| 5 | Wash solution | Phage binding | |
| 6 | | Lysis solution | Lysis solution |
| 7 | | IsOH solution | IsOH solution |
| 8 | | Silica capture/filtering | Silica capture/filtering |
| 9 | Wash solution | Wash solution | Wash solution |
| 10 | | Wash solution | Wash solution |
| 11 | | Elution solution | Elution solution |
| 12 | | | RT |
| 13 | | Ampligase ligase | Ampligase ligase |
| 14 | | Exo-I-III | Exo-I-III |
| 15 | | UNG | UNG |
| 16 | | primer | primer |
| 17 | | UNG | UNG |
| 18 | | Melting analysis probes | Melting analysis probes |

Fig. 7

SAMPLE MULTIPROCESSING

CROSS-REFERENCE TO RELATED APPLICATION

This application is the National Stage of International Application No. PCT/US2005/020095, filed Jun. 7, 2005, which claims the benefit of U.S. Provisional Patent Application Ser. No. 60/577,692, filed Jun. 7, 2004, which is hereby incorporated herein by reference in its entirety. The following U.S. patent applications are also hereby incorporated herein by reference in their entireties: Ser. Nos. 09/910,233; 09/782,732; 10/241,816; and 10/773,775.

INTRODUCTION

Many situations call for testing a single sample for multiple target agents. In addition, many situations call for testing multiple samples simultaneously, either all for the same target agent or for different target agents. Sample preparation is frequently required in performing diagnostic assays, food assays and environmental sample assays, particularly in the processing of biological samples. A biological sample, for instance, typically undergoes intensive, demanding processing before it is in condition suitable for an assay. Proper sample preparation often requires precise conditions, such as particular temperatures, concentrations, reagent volumes, and, especially, the removal of materials that can interfere with the desired assay. Frequently a raw sample must be removed to a distant location to receive proper processing by highly skilled personnel in a tightly controlled laboratory setting. Conventional processing devices and methods often require large, highly complex and sophisticated instrumentation. These factors of conventional sample processing necessarily cause a delay in the time to result, high costs, compromised sample integrity and limitations on the practicality of using diagnostic assays in many instances.

SUMMARY

The present disclosure provides devices and methods for multi-assay processing samples and processing multiple samples. The disclosed devices and methods can facilitate the preparation of samples and the performance of multiple assays through multiple processing steps.

In one aspect, a sample processing cartridge may include a plurality of segments arranged in an array at least two rows long and two columns wide. Each segment may be defined by at least one wall of the sample cartridge, fluidly isolated from adjacent segments at least in part by at least one breakable seal or by at least one permanent seal, so expandable as to receive a volume of fluid expelled from another segment, and so compressible as to contain substantially no fluid when so compressed. At least two adjacent segments of at least one row of the array may be aligned along a longitudinal axis of the row and have substantially the same height along a latitudinal axis of the row. At least two adjacent segments in at least one row may be separated by a permanent seal to form at least two tracks. At least one segment, or at least two adjacent segments separated by a breakable seal, may be in fluid communication with the at least two tracks. At least one segment may contain at least one reagent.

In another aspect, a method of processing sample may include introducing at least one sample into at least one segment of a plurality of segments arranged in an array at least two rows long and two columns wide. Each segment of the array may be fluidly isolated from adjacent segments at least in part by at least one breakable seal or by at least one permanent seal, so expandable as to receive a volume of fluid expelled from another segment, and so compressible as to contain substantially no fluid when so compressed. At least two adjacent segments in at least one row may be separated by a permanent seal to form at least two tracks. At least one segment may be a branch segment either in fluid communication with the at least two tracks or isolated from the two tracks by one or more breakable seals. The method may further include incubating the sample in a segment with a substance capable of specific binding to a preselected component of the sample, moving a fluid from a first segment to an adjacent second segment by compressing the first segment and propelling the fluid into the second segment, and splitting a fluid from a branch segment into the at least two tracks.

In yet another aspect, a method of processing sample may include introducing at least one sample into at least two tracks of a sample vessel having at least two tracks. Each track may be fluidly isolated from other tracks and discretized by breakable seals into a plurality of fluidly isolated segments. The method may further include incubating the sample in a segment of each track with a substance capable of specific binding to a preselected component of the sample, moving a fluid from first segment to an adjacent second segment by compressing the first segment and propelling the fluid into the second segment, and performing a first assay in the first of the two tracks and a second assay in the second of the two tracks.

BRIEF DESCRIPTION OF THE DRAWINGS

FIG. 7 is a schematic of an array of segments used for performing an aerosol sample test.

DETAILED DESCRIPTION

The present disclosure describes devices and methods for processing one or more samples for multiple assays. In several embodiments, sample processing cartridges with an array of segments provide a convenient vessel for receiving, storing, processing, and/or analyzing a biological sample in multiple assays. In certain embodiments, sample processing cartridges may provide a convenient vessel for receiving, storing, processing, and/or analyzing multiple biological samples. In certain embodiments, the cartridge may facilitate concurrent sample processing protocols involving multiple processing steps. In certain embodiments, a sample may be collected in a sample processing cartridge, and the cartridge then positioned in an analyzer; the analyzer may then manipulate the cartridge segments and its contents to process the sample.

A preferred embodiment includes a cartridge which has been segmented into an array of compartments by breakable and/or permanent seals. The individual segments may be so expandable as to receive a volume of fluid expelled from another segment, and so compressible as to contain substantially no fluid when so compressed. In some embodiments the tubule may be so expandable as to be capable of receiving a volume of fluid from each of multiple segments in one segment. This can allow sample and reagents to undergo certain processing steps in one segment, thereby leading to a simpler mechanical structure for performing assays. Another benefit of an embodiment using a segment that may be so expandable is that the same segment structure may be used to package different volumes of reagents within segments, allowing the same segment to be packaged in differing ways depending upon the assay to be performed.

In another preferred embodiment, segments are aligned such that substantially all and only the segments in a row of the array of segments are capable of being compressed simultaneously by an actuator of the analyzer. The alignment of segments in a row allows the parallel processing of samples within this row by one or a minimum number of actuator compressing across this row simultaneously without affecting other rows.

In another embodiment, tracks including a plurality of fluidly isolated segments form different pathways for processing a sample in different assays or for processing different sample in a particular assay. Segments within a track are connected by breakable seals. Segments in different tracks are isolated from one another by permanent seals.

Figure 1A:
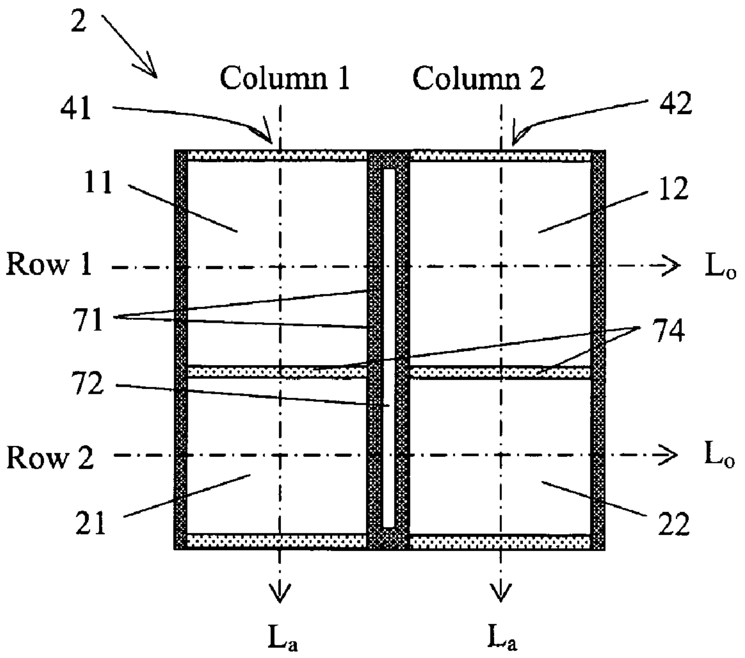
FIG. 1A is an exemplary embodiment of a two by two array of segments in a sample processing cartridge.

FIG. 1A shows one embodiment of a cartridge which has a two-row by two-column array of segments. The cartridge has a wall (not shown) which may be formed by one or more pieces of flexible material folded and/or welded or otherwise attached to one another. Each row in the array has a longitudinal axis, such as axis $L_o$, and a latitudinal axis, such as axis $L_a$. Segments 11 and 21 are connected by breakable seals 74 and form a first track 41. Segments 12 and 22 are connected by breakable seal 74 and form a second track 42. First track 41 is divided from second track 42 by permanent seal 71. In certain preferred embodiments, a cut-through slot 72 may separate permanent seals 71 between two fluidly isolated segments to allow the large expansion of a segment when accommodating a large volume of liquid and to allow radial freedom to avoid encumbering the track's radial movement as it is compressed.

Figure 1B:
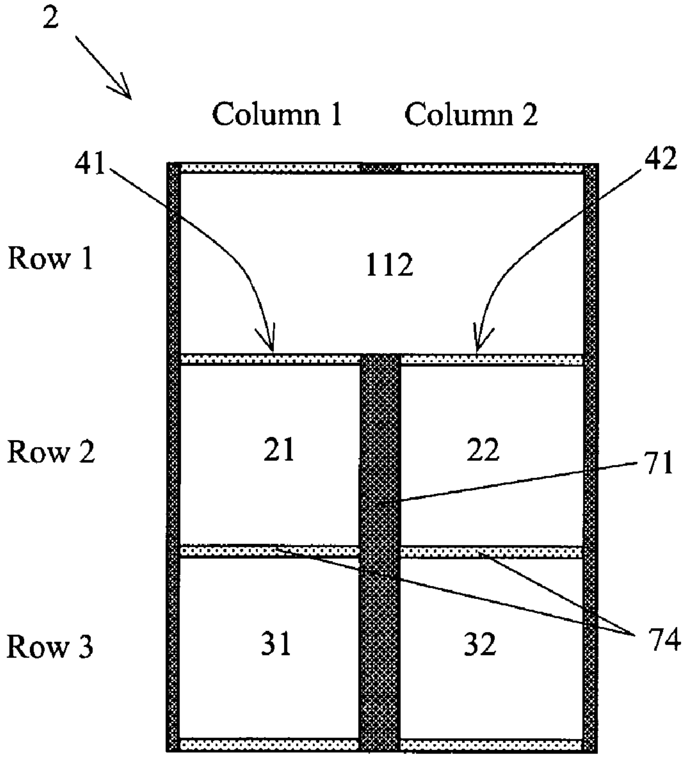
FIG. 1B is an exemplary embodiment of a two by three segment array in a sample processing cartridge.

FIG. 1B illustrates another embodiment, in which the sample processing cartridge may include a three-by-three array of segments. The two segments of the first row are merged forming a branch segment 112. Segments 21 and 31 are connected by breakable seals 74 and form a first track 41. Segments 22 and 32 are connected by breakable seal 74 and form a second track 42. First track 41 is divided from second track 42 by permanent seal 71. Branch segment 112 is in fluid communication with segment 21 and 22 of track 41 and 42 for splitting a sample into track 41 and 42 for parallel processing. In other embodiments, branch segment 112 may connected to segment 21 and 22 through a breakable seal.

In a preferred embodiment, one or more individual segments may contain various reagents and buffers for processing a sample. Clamps and actuators may be applied to the array of segments in various combinations and with various timings to direct the movement of fluid and to cause the breakable seals to burst. This bursting of the breakable seals may leave an inner cartridge surface that is substantially free of obstructions to fluid flow. In preferred embodiments, the flow of the biological sample may be directed toward the distal end of a track of the cartridge as the processing progresses, while the flow of waste may be forced to move in the opposite direction, toward the opening of the track where the sample was initially introduced. Waste may be stored in a segment of a cartridge proximal to the opening of the track.

In some embodiments, sample is introduced into a cartridge through a sample inlet. This sample inlet can be sealed, possibly permanently, by a cap with a locking mechanism, and a waste chamber may be located in the cap or in a segment. A significant benefit of this approach is that the processed sample does not come into contact with surfaces that have been touched by the unprocessed sample. Consequently, trace amounts of reaction inhibitors present in the unprocessed sample that might coat the walls of the cartridge are less likely to contaminate the processed sample.

Figure 2A:
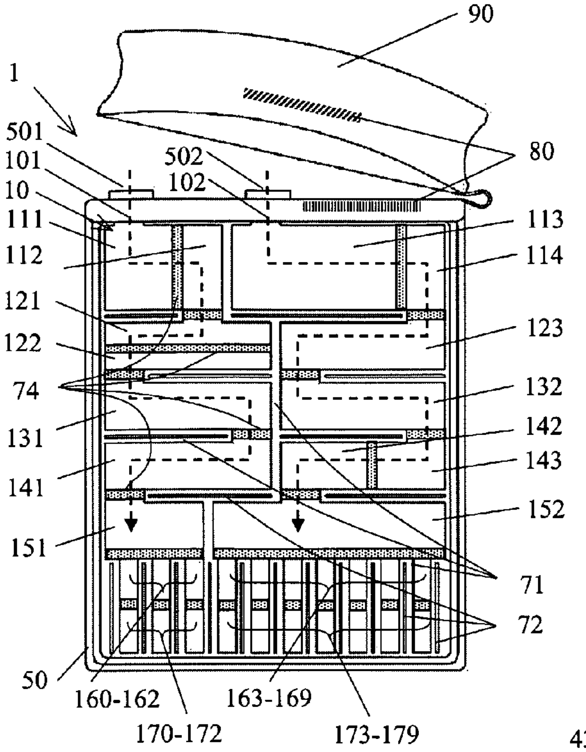
FIG. 2A is a front elevation view of an exemplary embodiment of a sample processing cartridge.
Figure 2C:
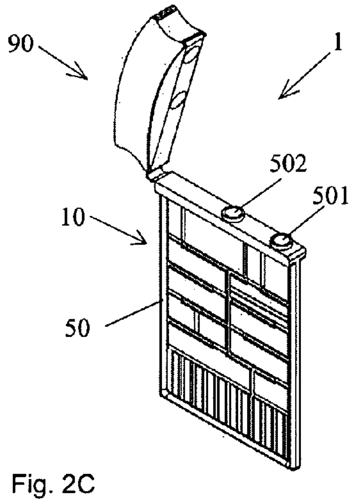
FIG. 2C is a perspective view of an exemplary embodiment of a sample processing cartridge.
Figure 2B:
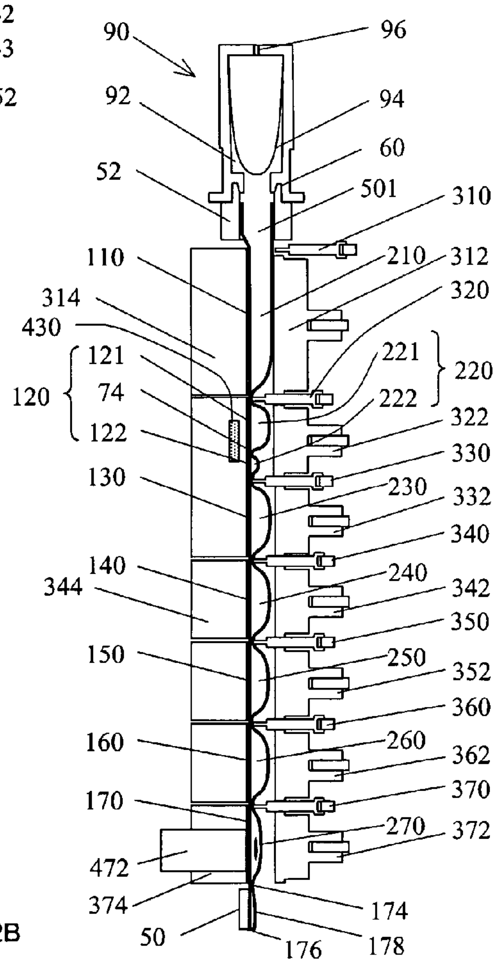
FIG. 2B is a cross sectional view of a sample processing cartridge positioned inside an analyzer.

The sample processing cartridge may include an array of segments 10 (FIGS. 2A-B). One or more segments may be transparent to light of at least a selected wavelength, to several wavelengths, to visible light, to infrared radiation, and/or to ultraviolet radiation. One or more segments may be flexible, or at least one part of the wall may be flexible, as described in more detail below. Segments such as 111, 112, 113, 114, 121, 122, 123, and/or 160-179, may be substantially flattened by compression. In an embodiment, an array of segments may have at least two tracks. In an embodiment, a track may have at least two segments. The flexible array of segments can provide operational functionality over a wide range of temperatures, such as between approximately 2° C. and 105° C., storage functionality over an even wider range, such as between −80° C. and 120° C., compatibility with samples, targets and reagents, low gas permeability, low water vapor transfer rate, minimal fluorescence properties, and/or resilience during repeated compression and flexure cycles. The array of segments may be made of a variety of materials, examples of which include but are not limited to: polyolefins such as polypropylene or polyethylene, polyurethane, polyolefin co-polymers, polychlorotrifluoroethylene (PCTFE), and/or other materials providing suitable characteristics. The array of segments properties, such as transparency, wetting properties, surface smoothness, surface charge and thermal resilience, may affect the performance of the cartridge. These proprieties may be improved through such exemplary processes as: seeding, plasma treating, addition of additives, and irradiation. In some embodiments, an additive material may be added to the plastic to improve selected characteristics. For example, a slip additive may be added, such as erucamide and/or oleamide; in some embodiment, a so-called "anti-block" additive may be added. An additive may have a concentration in the plastic in the range from about 0.01% to about 5.0%.

The tubule may be manufactured by a wide variety of suitable methods such as extrusion, injection-molding and blow-molding. In an embodiment the array of segments is formed by a tubule that is continuously extruded. Alternative techniques for manufacturing the array of segment include, e.g., casting, extruding, blowing, vacuum or thermal forming films that can be fashioned by secondary processing operations into a suitable shape. The array of segments wall material may include multiple layers by co-extrusion, or by film lamination. For example, an inner layer may be chosen for high biocompatibility and an exterior layer may be chosen for low gas permeability and low water vapor transfer rate. As a further example, the interior layer may be readily formed into a breakable seal 74, such as a peelable seal, while the exterior layer may be resilient and highly impermeable. For use in the present disclosure it is preferred the array of segments have a wall thickness of about 0.03 mm to about 0.8 mm, preferably 0.03 mm to about 0.5 mm, with the array of segments able to be substantially flattened with an applied exterior pressure on the order of 1 atmosphere.

In some embodiments, the apparatus may have toughened walls in at least one segment. This toughened wall may allow for the dislocation of clumps of cells from solid sample such as biopsy samples or solid environmental samples using smashing motions. In a further embodiment, the apparatus may have a flexible wall and a rigid wall to form at least a portion of the array of segments. The rigid wall may further include some features, such as a groove or a well, to forming a channel or micro-measuring-cup when two walls of the segment are contacted by compression. This rigid wall may also provide a frame functionality and a support to compress the segments.

The sample array of segment 10 may be partitioned into two tracks 101 and 102 including one or more segments. Track 101 may include segments 111, 112, 131, and 141, and/or sub-segments 121 and 122, and/or branch segment 151, and/or sub-tracks formed by segments 160 to 162 and 170 to 172, respectively. Track 102 may include segments 113, 114, 123, 132, 142, and 143, and/or branch segment 152, and/or sub-tracks formed by segments 163 to 169 and 173 to 179, respectively. In preferred embodiments, the tracks are defined by permanent seals 71 and segments within a track are defined by breakable seals 74 to fluidly isolate adjacent segments in a track. A sample can be input through a fist opening 501 of track 101 and a second opening 502 of track 102. Thereafter, waste from a processed sample may be moved back through the openings and stored in reservoir 92 in cap 90 while the target is pushed towards the opposite end, thereby minimizing contamination of the target by reaction inhibitors that may have become attached to the segment wall, and confining the target to a clean segment of the track which can contain suitable reagents for further operations of the target. In another embodiment, a sample can be input through an opening connect to a branch segment 112, and processed, then split into segment 21 of track 41 and segment 22 of track 42 for further processing.

Some embodiments may use a first track including a plurality of at least three segments, each containing at least one reagent. In some embodiments, these segments may contain reagents in the following order: the reagent in the second segment may be either a lysis reagent, a dilution or wash buffer, or a substrate; the reagent in the third segment may be either a substrate, a lysis reagent, a washing buffer or a neutralization reagent; the reagent in the fourth segment may be a wash buffer, a suspension buffer, an elution reagent, or nucleic acid amplification and detection reagents. In some embodiments, the three segments may be arranged continuously in a track, while in other embodiments, these three segments may be separated by another segment or segments in between.

Some embodiments may use a second track including a plurality of at least 2 segments, each containing at least one reagent. In some embodiments, these segments may contain reagents in the following order: the reagent in the second segment may be a substrate, a capture molecule, a detection substance and/or a dilution or wash buffer; the reagent in the third segment may be a substrate, a capture molecule, a detection substance, a washing buffer; the reagent in the fourth segment may be a wash buffer, a suspension buffer, a detection enhancer an elution reagent, a display molecule, or nucleic acid amplification, and detection reagents. In some embodiments, the three segments may be arranged continuously in a track, while in other embodiments, these three segments may be separated by another segment or segments in between. The detection substance can be: an antibody, and antibody conjugated to a fluorescent group, an antibody conjugated to a lanthanide chelate, an antibody conjugated to a nucleic acid, a bacteriophage or a virus displaying antibodies, proteins, or peptides, cells displaying antibodies, proteins, or peptides. Antibodies conjugated to nucleic acids, bacteriophage and cells displaying antibodies synthesized in vivo (and thus encoded by the bacteriophage, virus or cells) can be detected by a nucleic acid test.

In preferred embodiments, breakable seal feature can be useful in separating, for example, a dry reagent from a liquid reagent until it is appropriate to reconstitute the two to perform a specific assay, or for separating chemically reactive species until the reaction is desired. A breakable seal 74 may be formed in a region of the array of segments 10 where opposing walls have been substantially joined, but not joined so strongly as to prevent the walls from being later peeled apart without significantly marring the walls of the array of segments or the previously sealed surfaces. Such a seal may be termed a "peelable" seal and is a kind of breakable seal. Peelable seals may have a width in the range of about 0.2 mm to 5 mm, preferably about 0.5 mm to about 3 mm, most preferably about 0.8 to about 1.5 mm. In some embodiments, the seal band may vary in height or shape and/or be oriented at an angle transverse to the axis of the tubule; such variations can change the peel characteristics.

Breakable seals 74 can be created between opposing walls of the array of segments by applying a controlled amount of energy to the array of segments in the location where the peelable seal is desired. For example, a temperature controlled sealing head can press the walls of the array of segments at a specific pressure against a fixed anvil for a specific time interval. Various combinations of temperature, pressure and time may be selected to form a seal of desired size and peel-strength. Energy may be delivered, for example, by a temperature controlled sealing head maintained at a constant temperature between 105° C. and 140° C. to heat a polypropylene tubing material; an actuator capable of delivering a precise pressure between 3 and 100 atmosphere over the desired seal region; and a control system to drive the sequencing of the actuator to a specific cycle time between 1 and 30 seconds. Using this method, satisfactory seals have been created in polypropylene sheets to peel open when subjected to an internal pressure on the order of 1 atmosphere. Alternate techniques to deliver the sealing energy to the tubule include RF and ultrasonic welding.

In other embodiments, alternate wall materials and blends of materials for the array of segments can be used to optimize peelable seal performance. For example, two polypropylene polymers of differing melting temperature can be blended in a ratio such that the composition and melt characteristics are optimized for peelable seal formation. In addition to or in lieu of breakable seals 74, the array of segments can further have one or more pressure gates, which are capable of reversibly opening and closing during the operation of a test by applying a controlled force to a segment of the array of segments.

Figure 3A:
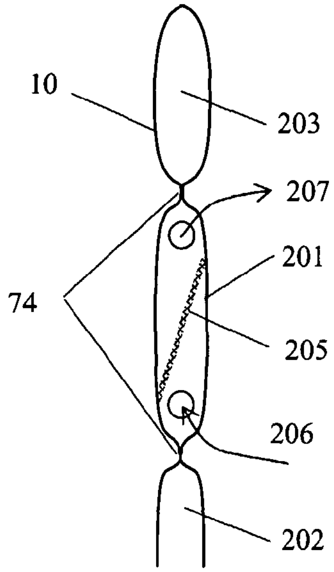
FIGS. 3A-B are, respectively, front and side elevation views of an exemplary embodiment of a sample processing cartridge.
Figure 3B:
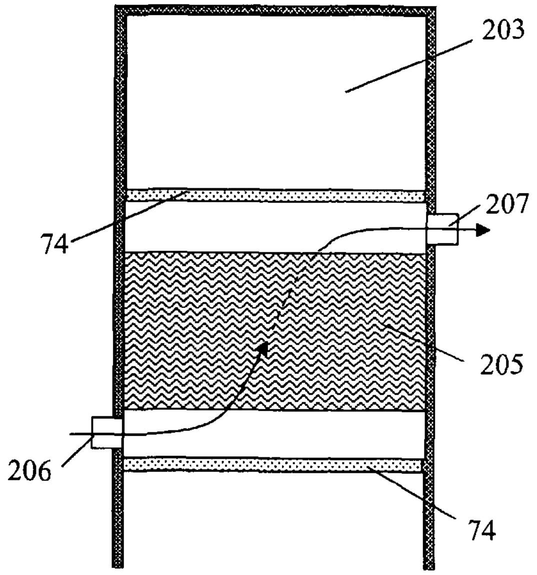

A filter can be embedded in a segment. In a preferred embodiment, a filter can be formed by stacking multiple layers of flexible filter material. The uppermost layer of the filter that directly contacts a sample may have a pore size selected for filtration; the bottom layer of the filter may include a material with much larger pore size to provide a support structure for the uppermost layer when a pressure is applied during filtration. In this preferred embodiment, the filter may be folded to form a bag, with the edges of its open end firmly attached to the wall of a segment. The segment with the filter bag may be capable of being substantially flattened by compressing the exterior of the array of segments. In another preferred embodiment, a segment 201 (FIG. 3A-B) may include a filter 205 and inlet 206 and outlet 207 flanking the filter 205. Segment 201 may further be flanked by segment 203 containing an elution buffer and at least one track 202. This configuration of segments allows the filtration of a fluid, such as air, moving through the filter from inlet 206 to outlet 207, followed by a backwash to elute the filtrate using the wash liquid in segment 203 through the filter and into track 202. A significant benefit of this approach is that the filter-captured targets in the sample may be detached from the filter and moved to the track for further processing.

In exemplary embodiments, one or more reagents can be stored either as dry substance and/or as liquid solutions in segments of the array of segments. In embodiments where reagents may be stored in dry format, liquid solutions can be stored in adjoining segments to facilitate the reconstitution of the reagent solution. Examples of typical reagents include: lysis reagent, elution buffer, wash buffer, DNase inhibitor, RNase inhibitor, proteinase inhibitor, chelating agent, neutralizing reagent, chaotropic salt solution, detergent, surfactant, anticoagulant, germinant solution, isopropanol, ethanol solution, antibody, nucleic acid probes, peptide nucleic acid probes, phosphothioate nucleic acid probes, aptamers and bacteriophage. In embodiments where one of the reagents is a chaotropic salt solution, a preferred component is guanidinium isocyanate or guanidinium hydrochloride or a combination thereof. In some embodiments, the order in which reagents may be stored in a track of the array of segments relative to the opening through which a sample is input, reflects the order in which the reagents can be used in methods utilizing the cartridge. In preferred embodiments, a reagent includes a substance capable of specific binding to a preselected component of a sample. For example, a substance may specifically bind to nucleic acid, or a nucleic acid probe may specifically bind to nucleic acids having particular base sequences. As another example, a substance may specifically bind to protein, or an antibody may specifically bind to protein having particular amino acid sequences.

In other exemplary embodiments, a solid phase substrate can be contained within a segment of an array of segments and used to capture one or more selected components of a sample (if such component is present in a sample), such as a target microorganism, nucleic acids, proteins or cells. Capturing can help to enrich the target component and to remove reaction inhibitors or interference components from a sample. Substrates may be liquid phase material or solid phase material which can capture target cells, virions, nucleic acids, proteins or other selected components under defined chemical and temperature conditions, and may release the components under different chemical and temperature conditions.

In some embodiments, a reagent can be a capture molecule, antibody, antigen, phage, receptor, and/or ligand, which bind to targets in a sample. The capture molecules may be labeled with an indicator molecule such as a donor fluorophor or an acceptor fluorophor, or a DNA. In some embodiments, a reagent can be a detection substance, second antibody, antigen, phage, receptor, receptor, and/or ligand, which bind the target or the capture molecules. The detection substance may be labeled with an indicator molecule such as a donor fluorophor or an acceptor fluorophor, or a DNA. The detection substance can be: an antibody, and antibody conjugated to a fluorescent group, an antibody conjugated to a lanthanide chelate, an antibody conjugated to a nucleic acid, a bacteriophage or a virus displaying antibodies, proteins, or peptides, cells displaying antibodies, proteins, or peptides. Antibodies conjugated to nucleic acids, bacteriophage and cells displaying antibodies synthesized in vivo (and thus encoded by the bacteriophage, virus or cells) can be detected by a nucleic acid test.

In some embodiments, a reagent can be coated on the substrate. Examples of coatable reagent are: receptors, ligands, antibodies, antigens, nucleic acid probes, peptide nucleic acid probes, phosphothioate nucleic acid probes, bacteriophages, silica, chaotropic salts, proteinases, DNases, RNases, DNase inhibitors, RNase inhibitors, and germinant solutions. In some embodiments, the substrate can be stored in a dry segment of the tubule while in other embodiments it can be stored immersed in a liquid. In some embodiments, the order in which reagents may be stored in the tubule relative to the substrate and the opening through which a sample is input, reflects the order in which the reagents and the substrate can be used in methods utilizing the apparatus.

The substrate can be: beads, pads, filters, sheets, and/or a portion of segment wall surface or a collection tool. In embodiments where the substrate is a plurality of beads, said beads can be: silica beads, magnetic beads, silica magnetic beads, glass beads, nitrocellulose colloid beads, and magnetized nitrocellulose colloid beads. In some embodiments where the beads can be paramagnetic, the beads can be captured by a magnetic field. Examples of reagents that may permit the selective adsorption of nucleic acid molecules to a functional group-coated surface are described, for example, in U.S. Pat. Nos. 5,705,628; 5,898,071; and 6,534,262, hereby incorporated herein by reference. Separation can be accomplished by manipulating the ionic strength and polyalkylene glycol concentration of the solution to selectively precipitate, and reversibly adsorb, the nucleic acids to a solid phase surface.

When these solid phase surfaces are paramagnetic microparticles, the magnetic beads, to which the target nucleic acid molecules have been adsorbed, can be washed under conditions that retain the nucleic acids but not other molecules. The nucleic acid molecules isolated through this process are suitable for: capillary electrophoresis, nucleotide sequencing, reverse transcription, cloning, transfection, transduction, microinjection of mammalian cells, gene therapy protocols, the in vitro synthesis of RNA probes, cDNA library construction, and the polymerase chain reaction (PCR) amplification. Several companies offer magnetic-based purification systems, such as QIAGEN's MagAttract™, Cortex Biochem's MagaZorb™, Roche Applied Science's MagNA Pure LC™, and MagPrep® Silica from Merck & Co. All of these kits use negatively charged particles and manipulate buffer conditions to selectively bind a variety of nucleic acids to the beads, wash the beads and elute the beads in aqueous buffers. Many of the products used by these companies use chaotropic salts to aid in the precipitation of nucleic acids onto the magnetic beads. Examples are described in U.S. Pat. Nos. 4,427,580; 4,483,920; and 5,234,809, hereby incorporated herein by reference.

Another aspect of this disclosure pertains to methods of increasing the reliability of a test by redundantly testing for a given analyte using reagents that detect different moieties of this analyte. In the case of nucleic acid tests, this usually involves identifying multiple sequence targets to design amplification primers and detection probes while in the case of proteins this usually involves identifying specific protein binding reagents, antibodies or peptides displayed on the surface of bacteriophage or cells, that recognize different epitopes on the protein. The use of a combination of different nucleic acid target sequence binding probes and primers as well as protein epitope-recognizing reagents to obtain redundant target detection is also envisaged. Such a combination of different analyte types in a battery of tests for a particular biological agent provides confirmation of measurements obtained from nucleic acid tests with protein tests and vise versa. A term commonly used by those familiar in the art to describe such cross analyte confirmation is "orthogonal" confirmation. A preferred embodiment is the use of orthogonal confirmation for diagnostic tests targeting RNA viruses, such as the human immunodeficiency virus (HIV) or the human hepatitis C virus (HCV). Indeed, these viruses are known to exist as mixed populations in individual human hosts (a.k.a., quasispecies). Those familiar with the art will know that the sample processing procedures required for nucleic acid tests and protein tests are significantly different.

In some embodiments the substrate may be a pad. In further embodiments, the substrate pad can include paper, alternating layers of papers with different hydrophobic properties, glass fiber filters, or polycarbonate filters with defined pore sizes. In some embodiments, the pad may be a filter or impermeable sheet for covering selected portion of the surfaces of the pad, said filter having a predetermined pore size. Such a filtration device can be used for separations of white blood cells and red blood cells (or other particles, such as virus or microorganisms) from whole blood and/or other samples. The pad can be mounted on a segment wall and/or on a sample collection tool. In some embodiments the pad can be soaked with a reagent solution while in other embodiments it may be coated with dry reagents.

In some embodiments, a pressure gate can be incorporated to selectively close and open an inlet opening of the cartridge or to selectively close and open a connection between two segments. An exemplary embodiment is to incorporate a check value into a segment to restrict the flow of liquid in one direction. In some embodiments, a pressure gate can be incorporated to selectively close and open a second opening, located at the distal end of the track, to collect the products generated during a test from the track for further processing, outside of the cartridge. In some embodiments, this second opening may located in a segment defined by two pressure gates 174 and 176 to store a product from the sample processing segments. In some embodiments, a combination of a breakable seal and a pressure gate may be provided for transferring the contents of the track to a second opening.

In some embodiments a cartridge closing device for closing the cartridge after sample input may include a cap 90 (FIG. 2A-2B) and/or clamp 310. An interface or adaptor 60 between the cap and the first opening of the array of segments may be used to ensure a secure, hermetic seal. In an exemplary embodiment, this interface may be threaded and may include tapered features on the cap and/or a suitably rigid tube frame 50 such that, when fastened together, the threads can engage to mate the tapered features between the tube frame and cap to provide a suitable lock. In other embodiments the cap locking device may include snap fits, press fits, and/or other types of "twist and lock" mechanism between the cap and tube holder, and similar arrangements in which the cap is permanently attached to the tubule, such as by hinging or tethering the cap.

Both the cap 90 and cartridge frame 50 can be made of a suitable injection molded plastic such as polypropylene. The cartridge frame 50 can, in turn, be fastened to the flexible array of segments by a permanent, hermetic seal. The exterior portion of the cap may be covered with ridges or finger grips to facilitate its handling. Furthermore, the cap 90 may include an area for attaching a sample identification mark or label 80. As a further alternative, the cap may be directly attached to the openings of the array of segments through a press fit or a collar that compresses the flexible tube opening against a protrusion in the cap to create a hermetic seal. The lock between the cap and cartridge frame may be keyed or guided such that a collection tool or features integrated into the cap can be definitively oriented with respect to the cartridge to facilitate sample processing and the flattening of the array of segments. Furthermore, the cap may incorporate features such as a ratchet or similar safety mechanism to prevent the cap from being removed after it has been installed onto the opening of the array of segments of the cartridge.

The cap 90 used to close the array of segments in some embodiments may contain a cavity 92 within it by making the cap body substantially hollow. In some embodiments, the hollow portion extends from the top of the cap body to an orifice at the base of the cap body. To form a chamber, the top of the cavity may be closed by fastening a cover onto the cap body. The cover may be constructed of the same piece as the cap body. The cover may incorporate a vent hole 96 or may further incorporate an affixed microbe barrier, filter or a material that expands to close off the vent hole when exposed to a liquid or specific temperature. The bottom of the chamber may be left open or closed by a breakable septum or valve. The hollow chamber may further incorporate a flexible membrane or septum 94. This flexible septum could be manufactured using dip molding, liquid injection silicone molding, blow molding, and/or other methods suitable for the creation of thin elastomeric structures. The flexible septum can be inserted into the cap body cavity 92 assembly so as to effectively isolate the interior portion of the cartridge from the exterior environment after the cap is in place on the array of segments. The flexible septum could be designed such that, in the absence of externally applied pressures, its inherent stiffness ensures it is in a preferred, known state of deformation. As a further embodiment, the flexible septum may be replaced by a plunger. In an exemplary embodiment, a cap body may be injection molded of a suitable thermoplastic and contain an interior cavity having at least a volume capable of accepting waste fluids generated during the assays in the cartridge. The chamber in the cap body could be adapted for useful purposes such as holding or dispensing a reagent, serving as a reservoir to hold waste fluids, serving as a retraction space for an integrated collection tool, or a combination of thereof.

The cap 90 may have an integrated collection tool such as a swab, capillary tube, liquid dropper, inoculation loop, syringe, absorbent pad, forceps, scoop or stick to facilitate the collection of liquid and solid samples and their insertion into the cartridge. The collection tool may be designed to collect and deposit a predetermined amount of material into the cartridge. Reagents may be stored on the collection tool itself. For example, the collection tool may include a swab impregnated with a dry salt such that when the swab is hydrated it would suspend the salt off the swab into solution. Furthermore, the collection tool and cap may be designed such that the collection tool portion retracts into the cap body after depositing the sample into the cartridge to leave the segments of the array of segments substantially unencumbered.

The chamber 92 in the cap may be fashioned to store a reagent. To accomplish this, for example, the base of the chamber may be closed by a breakable septum or valve (not shown) such that when the cap is squeezed, the septum breaks to release the reagent. Such a feature would be useful, for example, if the cap were integrally formed with a collection tool such as a swab or stick. In this instance, the reagent released from the cap chamber could be used to wash a sample off the collection tool into a tube segment or to lyse the sample contained on the collection tool. Reagents may also be released from the cap chamber by opening the breakable septum using pressure generated by compressing a flexible segment of the array of segments to force fluid from the segment up into the cap chamber. The chamber in the cap may be fashioned to store waste fluids derived from processing within the tubule. In a preferred embodiment, the base of the chamber may be left open such that when connected to the first opening of the array of segments, a fluid passage is formed between the tracks in the array of segments and the chamber. As fluid is moved into the cap chamber, the flexible septum 94 contained within can move from an initial position upward so as to accommodate the influx of new fluid. This septum movement can be facilitated by the incorporation of a vent hole 96 on the cap body cover.

After fluid has been transferred into the cap chamber a clamp 310 or actuator 312 can act to compress the segment and effectively seal off the cap chamber volume from the tubule segments. As an alternative embodiment, the cap chamber may incorporate a pressure gate or check valve (not shown) to prohibit fluid flow from the cap chamber back into the segments. As a further alternative, the flexible septum may be omitted with the cap chamber cover including a microbe barrier to permit the free escape of contained gasses but retain all the liquid volumes and infectious agents in the segments. As a further alternative, the flexible septum can be replaced with a plunger that would move axially upward to accommodate additional fluid volumes transferred from the segments to the cap chamber. Other methods to accommodate fluidic waste within the cap chamber can be readily envisioned without departing from the scope of the present disclosure.

A substantially rigid frame 50 may be provided to hold the flexible array of segments 10 suitably taught by constraining at least the two distal ends of the array of segments. In an exemplary embodiment, a first constraint may be provided to permanently attach and seal the array of segments to the frame around the sample inlet openings of the array of segments. This seal may be created by welding the flexible array of segments to the frame using thermal and/or ultrasonic sources. Alternatively, the seal may be created using a hot-melt adhesive joint with ethylene vinyl acetate, or by making a joint using a UV cure epoxy or other adhesives. In further embodiments, the array of segments may be mechanically sealed or insert-molded with the frame. A second constraint may be provided to attach and seal the array of segments to the base of the frame. In an exemplary embodiment of this second constraint, this end of the array of segments may be sealed flat and attached to the rigid frame by thermal and/or ultrasonic welding techniques. Alternatively, this joint and seal may also be formed using adhesive or mechanical approaches. In an alternative embodiment, the second seal may be similar to the first seal, being substantially open to enable access to the contents of the flexible array of segments from the second opening. The array of segments and frame materials can be optimized for joint manufacture. For example, the frame can be made of polypropylene having a lower melting point than the thinner tubule to ensure more uniform melting across one or more weld zones. To facilitate welding between the array of segments and the frame, the joint area may be tapered or otherwise shaped to include energy directors or other commonly used features enhance weld performance. Third and/or fourth constraints may be provided to attach and seal the array of segments to the base of the frame. In an exemplary embodiment of these third and fourth constraints, two side ends of the array of segments may be sealed flat and attached to the rigid frame by thermal welding, ultrasonic welding, and/or other techniques. In an exemplary embodiment, the rigid frame can be made of any suitable plastic by injection molding.

The rigid frame 50 can incorporate several features to facilitate the compression and flattening of the flexible array of segments. For example, in an exemplary embodiment, the flexible array of segments 10 may be constrained only at its two axial extremities to allow maximum radial freedom to avoid encumbering the array's radial movement as it is compressed. In another embodiment, compression may be facilitated by including a relief area in the frame, near the opening of the array of segments. This relief area may be used to facilitate the flexible array's transition from a substantially compressed shape in the segments to a substantially open shape at the opening. Other useful features of the rigid frame that can facilitate the compression of the flexible array of segments may include an integral array tensioning mechanism. In an exemplary embodiment, this tension mechanism could be manufactured by molding features such as cantilever or leaf type springs directly into rigid frame to pull the array of segments taught at one of its attachment points with the frame.

The rigid frame 50 can facilitate tube identification, handling, sample loading and interfacing to the cap. For example, the frame can provide additional area to identify the cartridge through labels or writing 80 affixed thereto. The plastic materials of the frame may be color coded with the cap materials to help identify the apparatus and its function. The frame may incorporate special features such as changes in thickness or keys to guide its orientation into a receiving instrument or during manufacture. The frame may interface to a sleeve 90 or packaging that covers or protects the flexible array of segments from accidental handling damage, light exposure, and/or heat exposure. The body of the rigid frame may also provide a convenient structure to hold the array of segments. The frame may have an integral collection tool such as a deflector or scoop to facilitate sample collection into the apparatus. The sample-receiving end of the frame may also incorporate a tapered or funneled interior surface to guide collected sample into the opening of the array of segments.

In another embodiment, a plurality of arrays of segments may be connected in a chained tape format. In certain preferred embodiments, the tape of arrays of segments may be rolled into reels and housed in a cassette, wherein unused arrays of segments are stored in a first reel while spent arrays of segments are stored in a second reel. Tests are performed on the exposed array of segments connecting two reels. This allows the storage of multiple array of segments in one convenient format, especially for automated repeat testing at certain time intervals, where a unused array of segments may be indexed forward to accept and process a sample.

In some embodiments, a method of processing a sample by using the apparatus described herein is contemplated. In certain embodiments, the sequence of events in such test may include: 1) collecting a sample using a collection tool, 2) introducing the collected sample into a cartridge, which can include a flexible array of segments that may contain the reagents required during the test, 3) processing the sample by capturing a preselected component of the sample, 4) splitting the processed sample into a plurality of fluidly isolated tracks, and 5) detecting a preselected component in at least one track. For example, this sequence of events can be used to characterize a sample using a plurality of assays, such as immunoassay, nucleic acid assay, and cellular assay. Alternatively, this sequence of events can be used to genotype a sample at a plurality of loci, wherein the genotyping of a single loci occurs in each track, In another embodiment, the sequence of events in such a test may include: 1) collecting multiple samples; 2) introducing the collected samples into respective tracks of a cartridge, wherein each track may contain the reagents required for a single type of assay; 3) detecting a preselected component in at least one track of the cartridge. In certain embodiments, the sequence of events may further include processing the sample by capturing a preselected component of the sample. For example, this sequence of events can be used to genotype the same loci for a variety of biological samples, wherein each sample is genotyped in a single track.

The preselected component detected in a track may be a nucleic acid, a protein, a lipid, a carbohydrate, a metabolite, a cell, a bacterium, a microorganism, or a virus. In certain preferred embodiments, the preselected components in a single track may be multiple targets using a similar assay protocol. In certain preferred embodiments, the preselected component or components detected in each track is or are the same for a plurality of tracks. In other preferred embodiments, the preselected component or components detected in each track is or are different for a plurality of tracks.

In another preferred embodiment, a track is further split into sub-tracks for further processing. For example, a first track of a cartridge may be used to detect protein toxins and a second track may be used to detect bacteria. In the first track, toxins may be purified and split into a plurality of sub-tracks for immunoassay detection of individual toxins. In the second track, nucleic acids may be extracted from a sample and split into a plurality of sub-tracts for spatially multiplexed PCR amplification to detect single bacteria species.

In some embodiments, fluids from a plurality of segments may be merged into one branch segment. For example, different nucleic acid targets may be amplified in a plurality of tracks, and the amplicons from the plurality of tracks may be pooled into one segment for microarray analysis.

In exemplary embodiments, the flow of the sample may be from the opening towards the distal end of the track as the test progresses while the flow of waste may be towards the closed sample input opening of the track, where a waste chamber in the cap of the cartridge receives the waste for storage. In an alternative embodiment, the sample and waste are split into two respective tracks, and the waste may be stored in the waste track. Consequently, undesirable contact between a processed sample and surfaces in a reaction vessel that have been touched by the unprocessed sample is avoided, thereby preventing reaction inhibition due to trace amounts of reaction inhibitors present in the unprocessed sample and that might coat the walls of the reaction vessel.

In some embodiments, a method of extracting nucleic acids from biological samples by using the apparatus described herein is contemplated. In certain embodiments, the sequence of events in such a test may include: 1) a biological sample or biological sample collected with a collection tool, 2) a sample processing cartridge, which can include a flexible array of segments that may contain the reagents required during the test, and in which the collected samples can be placed using at least an opening in the array of segments, 3) at least one substrate that may be set at a controlled temperature and/or other conditions to capture target organisms or nucleic acids during a set incubation period, 4) organisms or molecules, in the unprocessed sample, that may not bind to the substrate and could thus be removed by transferring liquid to a waste reservoir, 5) storing waste, in a waste reservoir, that can be segregated from the target by a clamp and/or actuator compressed against the array of segments, 6) a wash buffer, released from another segment of the cartridge, that can remove reaction inhibitors, 7) an elution reagent, from another segment, that can release the target bound to the substrate after incubation at a controlled temperature, and 8) nucleic acids that can be detected by techniques well known to those familiar in the art or collected through a second opening in the tubule. In exemplary embodiments the flow of the sample may be from the opening towards the distal end of the array of segments as the test progresses while the flow of waste may be towards the closed sample input opening of the array of segment, where a waste chamber in the cap of the cartridge receives the waste for storage. Consequently, undesirable contact between a processed sample and surfaces in a reaction vessel that have been touched by the unprocessed sample is avoided, thereby preventing reaction inhibition due to trace amounts of reaction inhibitors present in the unprocessed sample and that might coat the walls of the reaction vessel.

Some embodiments may incorporate the use of a sample processing cartridge 1, with a flexible array of segments 10, such as segments 11, 12, 21, 22, 31, 32, 112, 111, 112, 113, 121, 122, 123, 131, 132, 141, 142, 143, 151, 152, 160-169, and/or 170-179, that may be aligned such that substantially all and only the segments in a row are capable of being compressed simultaneously; and may contain reagents, such as reagents 212, 214, 221, 222, 223, 231, 232, 241, 242, 243, 251, 252, 260-269 and/or 270-279; as well as an analyzer, that may have a plurality of actuators, such as actuators 312, 322, 332, 342, 352, 362, and/or 372, clamps, such as clamps 310, 320, 330, 340, 350, 360, and/or 370, and blocks, for example 314, 344, and/or 374 (others unnumbered for simplicity); opposing the actuators and clamps, to process a sample. Actuators may span substantially the entire height and width of a row of the array of segments to cross all the tracks for parallel processing of segments within a row. Alternatively, actuators may span a portion of the width of a row of the array of segments, wherein a plurality of actuators aligned with segments of a row may process segments of the row crossing different tracks independently. Various combinations of these actuators, clamps, and/or blocks may be used to effectively clamp the array of segments closed thereby segregating fluid. In exemplary embodiments, at least one of said actuators or blocks may have a thermal control element to control the temperature of a segment or segments for sample processing. The sample processing apparatus can further have at least one magnetic field source 430 capable of applying a magnetic field to a segment. The sample processing apparatus can further have a detection device 472, such as photometer or a CCD, to monitor a reaction taking place or completed within the array of segments.

The combined use of the array of segments and the analyzer can enable many sample processing operations. Collecting a sample, such as blood, saliva, serum, food, water, soil, tissue biopsy, stool or other solid or liquid samples, can be accomplished by using a sample collection tool. A sample collection tool may be incorporated into the cap 90. After a suitable amount of the sample has been collected, the cap can be placed onto the opening of the array of segment to close the array and deposit the sample into the first segment. Following this step, the sample contained on the collection tool or deposited into the segment may be washed off or re-suspended with reagents contained in a second segment or separate chambers within the cap by compressing a potion of the cap. The cartridge can then be loaded into the analyzer for further processing. Identification features, such as a barcode or an RF tag, can be present on the cartridge to designate the sample's identity in a format that can be read by the analyzer and/or a user.

Opening a breakable seal of a segment can be accomplished by applying pressure to the adjacent segment to irreversibly separate the bound surfaces of the wall of the array of segments. An actuator can be used to apply the required pressure to compress a segment containing fluid to open a breakable seal. In embodiments where a segment is delimited by two breakable seals, A and B, the analyzer may preferentially break seal A by physically protecting the seal B region with an actuator or clamp to prevent seal B from breaking while pressure is applied to the segment to break seal A. Alternatively, seal A may be preferentially opened by applying pressure to the segment adjacent to seal A in a precise manner such that; seal A is first opened by the pressure created in the adjacent segment; after seal A is broken, the pressure between the two segments drops substantially due to the additional, combined, segment volume; the reduced pressure in the combined segment is insufficient to break seal B. This method can be used to open breakable seals one at a time without using a protecting actuator or clamp. As a further alternative, the adherence of seal A may be inferior to that of seal B such that seal A can break at a lower pressure than seal B.

A process of moving fluid from one segment to another segment may include, for example, releasing a clamp on one end of the first segment, compressing a clamp on the other end of the first segment, releasing an actuator on the second segment, and compressing an actuator on the first segment to move the liquid from the first segment to the second segment. Alternatively, the clamp may be omitted or be opened after releasing the actuator on the second segment.

A process of splitting fluid from a branch segment to a plurality of tracks may include, for example, compressing the receiving segments of the plurality of tracks, decompressing said receiving segments to define a gap to control the volume of said segment, compressing the branch segment to fill the receiving segments of a plurality of track with a defined volume, and clamping the interface between the branch segment and the receiving segment of each track. The volume filled into a receiving segment may be controlled by the width of a receiving segment at its interface with the branch segment.

A process of merging fluid from a plurality of tracks into a branch segment, may include, for example, compressing the segments of a plurality of tracks, thereby bursting breakable seals to flow the liquids to the branch segment.

A process of mixing two substances, where at least one is liquid, located in adjacent segments may be accomplished by: releasing the clamp between the two segments, moving the liquid contained in the first segment, through an opened breakable seal to the second segment; and alternatively compressing the second segment and the first segment to flow the liquid between the segments.

An agitation can be performed by alternatively compressing and decompressing a segment with an actuator, while both clamps that flank the actuator are compressing the ends of the segment. In another embodiment, agitation can be achieved by alternatively moving liquid between at least two segments.

In embodiments where a segment may contain a liquid having a volume exceeding the volume required for a protocol, a process of adjusting the volume of the liquid in the segment can be executed by: compressing the segment to reduce the gap of between the walls of the array of segments to set the volume of the segment to a desired level and allowing the exceeding liquid to flow to the adjacent segment, past a clamp at the end of the segment or adjacent actuator; closing the segment with the clamp or actuator, resulting in an adjusted volume of liquid remaining in the segment.

A process of removing air bubbles may include agitating a segment containing the bubbly liquid. Another process of removing air bubbles may include agitating a first segment containing liquid while closing a second segment; opening the second segment and moving the liquid from the first segment to the second segment; agitating the second segment and adjusting a position of the second actuator to move the liquid-air interface near or above the upper end of the second segment, then clamping the upper end of the second segment to form a fully liquid-infused segment without air bubbles.

A dilution process can be conducted by using the liquid movement process wherein one of the segments includes a diluent and the other includes a substance to be diluted.

A process of reconstituting a reagent from dry and liquid components separately stored in different segments or sub-segments may include compressing the segment or sub-segment containing the liquid components to open the breakable seal connecting to the dry reagent segment, moving the liquid into the dry reagent segment or sub-segment, and mixing the dry reagent and liquid components using the mixing process.

Filtration can be performed by using a filter positioned between two segments or two sub-segments. For example, a whole blood sample can be deposited into a first segment with a filter bag. A pore size of the filter can be selected for blood cell filtration. A clamp can then close the end of the segment opposite to the filter bag, and an actuator can compress the first segment to generate pressure to drive plasma flow through the filter into a second segment. In another embodiment, a coagulation, aggregation or agglutination reagent, such as antibody against red cell surface antigens, a red cell coagulate, can be used to induce red cell-red cell binding to form clusters prior to the filtration. The pore size of the filter can be selected to block the clusters while allowing non-aggregated cells to flow through. Applying pressure on the first segment containing red cell clusters and blood can enrich the white cells in the second segment.

In an alternative embodiment, filtration can be performed by using a segment 201 (FIG. 3A-3B) including a filter 205 dividing the segment into a section A and a section B. Section A may further include an inlet 206, and section B may further include an outlet 207. For example, a pore size of the filter can be selected for filtration of microbial or toxin particles in air. An air sample can be passed through inlet 206 and filter 205 and out outlet 207, thereby depositing particles in section A of segment 201. The inlet 206 and outlet 207 are then closed by clamping or other mechanical means. An actuator of the analyzer compresses segment 203 to burst breakable seal 74 and release wash liquid into segment 201. A clamp closes the end of segment 203 and another actuator compresses segment 201, urging the wash liquid through filter 205 from section B to section A in segment 201, bursting breakable seal 74, and passing the wash liquid with sample particles to track 202 for further processing.

In some embodiments, a grinding process can be conducted by using an actuator to alternately compress and decompress a segment having a toughened wall with a micro-teeth-like inner surface, and thus break-up a solid sample, such as biopsy tissue sample, within the segment. In another embodiment, small glass beads can be used with the solid sample to improve the performance of grinding. In a further embodiment, a grinding wheel driven by a motor can be used to form a rotational grinding onto the sample in the segment and drive the movement of glass beads and a biological sample to improve grinding performance. The temperature of a liquid reactant in the segment can be selected so as to improve the grinding result.

Incubation of the contents in a segment can be achieved by setting the corresponding actuator and/or block temperature and applying pressure to the segment to ensure a sufficient surface contact between the wall of the segment and the actuator and the block, and bring the contents of the segment to substantially the same temperature as the surrounding actuator and/or block temperature. The incubation can be conducted in all processing conditions as long as the temperatures of all involved segments are set as required.

Rapid temperature ramping for incubation can be achieved by incubating a fluid in a first segment at a first temperature and setting a second temperature for a second segment adjoining the first segment, after incubation at the first temperature is finished, liquid is rapidly moved from the first segment to the second segment and incubated at the second temperature.

A flow driving through a flow-channel process can be performed by compressing a centrally-positioned segment with an actuator, and its flanking clamps if any, to form a thin-layer flow channel with a gap of about 1 to about 500 μm, preferably about 5 to about 500 μm through segment. The adjacent actuators compress gently on the adjacent segments in liquid communication with the flow-channel to generate an offset inner pressure to ensure a substantially uniform gap of the thin-layer flow channel. The two flanking actuators can then alternatively compress and release pressure on their respective segments to generate flow at controlled flow rate. Optional flow, pressure, and/or force sensors may be incorporated to enable closed-loop control of the flow behavior. The flow-channel process can be used in washing, enhancing the substrate binding efficiency, and detection.

A magnetic bead immobilization and re-suspension process can be used to separate the beads from the sample liquid. The magnetic field generated by a magnetic source 430 (FIG. 1B) may be applied to a segment 121, 122, and 123 containing a magnetic bead suspension 220 and 223 to capture and immobilize the beads to the segment wall. An agitation process can be used during the capturing process. In another embodiment, a flow-channel can be formed on the segment with the applied magnetic field, and magnetic beads can be captured under flow to increase the capturing efficiency. For re-suspending immobilized beads, the magnetic field may be turned off or removed, and an agitation or flow-channel process can be used for re-suspension.

A washing process to remove residual debris and reaction inhibitors from a substrate may be conducted by using three basic steps: First an actuator can compress a segment containing the substrate, such as immobilized beads or a sheet, to substantially remove the liquid from this segment. Second, a washing buffer may be moved to the segment by using a process similar to that of reconstituting a reagent from dry and liquid components. For bead-based substrates, a bead re-suspension process can be used followed by bead re-capture on the tubule wall. Third, after a mixing or agitation process, the actuator can compress the segment to remove the used wash liquid from the segment. In another embodiment, a flow-channel can be formed in the segment containing a substrate, which may be either immobilized beads or a sheet. A unidirectional flow wash, having laminar characteristics, is generated through the flow channel with the substrate. Finally, all the actuators and clamps, if any, can be closed to remove substantially all the liquid from the segments. In a further embodiment, a combination of the dilution based washing and the laminar flow based washing can be used to further enhance the washing efficiency.

Lysis can be achieved by heating a sample at a set temperature or by using a combination of heat and chemical agents to break open cell membranes, cell walls or uncoat virus particles. In another embodiment, lysis can be achieved using a chemical reagent, such as proteinase K, and a chaotropic salt solution. Said chemical reagents can be stored in one of more segments and combined with the sample using the processes disclosed above. In some embodiments, multiple processes such as chemical cell lysis, mechanical grinding and heating, can be combined to break up solid sample, for example tissue collected from biopsy, to maximize the performance.

Capturing target micro-organisms can be achieved by using a substrate. In an embodiment, the surface of the substrate may be coated with at least one binding reagent, such as an antibody, ligand or receptor against an antigen, receptor or ligand on the surface of the target organism (ASA), a nucleic acid (NA), a peptide nucleic acid (PNA) and phosphothioate (PT) nucleic acid probe to capture a specific nucleic acid target sequence complementary to the probe or a target organism. In another embodiment, the surface may be selected to have, or coated to form, an electrostatically charged (EC) surface, such as silica- or ion exchange resin-coated surface, to reversibly capture substantially only nucleic acids. In some embodiments, the substrate may be pre-packed in a segment or sub-segment in dry format, and a liquid binding buffer may be packed in another segment. The substrate and the buffer can be reconstituted by using the aforementioned processes.

In some embodiments, a reagent from an adjoining segment can be used to dilute the sample before incubation with the substrate. In some embodiments, the target organisms can be captured to the substrate prior to lysing the microorganisms; while in other embodiments, a lysis step can be conducted before the target capturing step. In preferred embodiments, incubation of the substrate in agitation can be conducted at a desired temperature, for example, at 4° C. for live bacterial capture, or room temperature for viral capture. Capture can be followed by a washing process to remove the residues and unwanted components of the sample from the tubule segment.

In some embodiments, magnetic beads can be used as the substrate for capturing target, and a magnetic bead immobilization and re-suspension process may be used to separate the beads from the sample liquid. In other embodiments where the substrate may be a pad or a sheet, the substrate pad and sheet may be incorporated into the collection tool and/or may be adhered on the tubule wall in a segment.

Elution can be achieved by heating and/or incubating the substrate in a solution in a tubule segment at an elevated temperature. Preferred temperatures for elution are from 50° C. to 95° C. In another embodiment, elution may be achieved by changing the pH of the solution in which the substrate is suspended or embedded. For example, in an exemplary embodiment the pH of the wash solution can be between 4 and 5.5 while that of the elution buffer can be between 8 and 9.

A spore germination process can be conducted by mixing a sample containing bacterial spores with germination solution, and incubating the mixture at a suitable condition. The germinant solution may contain at least one of L-alanine, inosine, L-phenylalanine, and/or L-proline as well as some rich growth media to allow for partial growth of the pre-vegetative cells released from the spores. Preferred incubation temperatures for germination range from 20° C. to 37° C. By coating the substrate with an anti-spore antibody, vegetative cells can be selectively enriched from a sample that contains both live and/or dead spores. The live spores can release a plurality of vegetative cells from the substrate, which can be further processed to detect nucleic acid sequences characteristic of the bacterial species. In some embodiments, the germinant solution can be absorbed in a pad.

In certain embodiments, nucleic acids extracted from the biological samples may be further processed by amplifying the nucleic acids using at least one method from the group: polymerase chain reaction (PCR), rolling circle amplification (RCA), ligase chain reaction (LCR), transcription mediated amplification (TMA), nucleic acid sequence based amplification (NASBA), and strand displacement amplification reaction (SDAR). In some embodiments, the nucleic acids extracted from the organism can be ribonucleic acids (RNA) and their processing may include a coupled reverse transcription and polymerase chain reaction (RT-PCR) using combinations of enzymes such as Tth polymerase and Taq polymerase or reverse transcriptase and Taq polymerase. In some embodiments, nicked-circular nucleic acid probes can be circularized using T4 DNA ligase or Ampligase™ and guide nucleic acids, such as DNA or RNA targets, followed by detecting the formation of the closed circularized probes after an in vitro selection process. Such detection can be through PCR, TMA, RCA, LCR, NASBA or SDAR using enzymes known to those familiar with the art. In exemplary embodiments, the amplification of the nucleic acids can be detected in real time by using fluorescent-labeled nucleic acid probes or DNA intercalating dyes as well as a photometer or charge-coupled device in the molecular analyzer to detect the increase in fluorescence during the nucleic acid amplification. These fluorescently-labeled probes use detection schemes well known to those familiar in the art (i.e., TaqMan™, molecular Beacons™, fluorescence resonance energy transfer (FRET) probes, Scorpion™ probes) and generally use fluorescence quenching as well as the release of quenching or fluorescence energy transfer from one reporter to another to detect the synthesis or presence of specific nucleic acids.

A real-time detection of a signal from a tubule segment can be achieved by using a sensor 472 (FIG. 1B), such as a photometer, a spectrometer, a CCD, connected to a block, such as block 470. In exemplary embodiments, pressure can be applied by an actuator 372 on the tubule segment 170 to suitably define the tubule segment's shape. The format of signal can be an intensity of a light at certain wavelength, such as a fluorescent light, a spectrum, and/or an image, such as image of cells or manmade elements such as quantum dots. For fluorescence detection, an excitation of light from the optical system can be used to illuminate a reaction, and emission light can be detected by the photometer. To detect a plurality of signals having specific wavelengths, different wavelength signals can be detected in series or parallel by dedicated detection channels or a spectrometer.

The disclosed devices and methods can be widely applied in the practice of medicine, agriculture and environmental monitoring as well as many other biological sample testing applications. Nucleic acids isolated from tissue biopsy samples that surround tumors removed by a surgeon can be used to detect pre-cancerous tissues. In these applications, hot-spot mutations in tumor suppressor genes and proto-oncogenes can be detected using genotyping techniques well known to those familiar with the art. Pre-cancerous tissues often have somatic mutations which can readily be identified by comparing the outcome of the genotyping test with the biopsy sample to the patient's genotype using whole blood as a source of nucleic acids. Nucleic acids isolated from white blood can be used to detect genetic variants and germline mutations using genotyping techniques well known to those familiar with the art. Examples of such mutations are the approximately 25 known mutants of the CFTR gene recommended for prenatal diagnosis by the American College of Medical Genetics and the American College of Obstetricians and Gynecologists. Examples of genetic variants are high frequency alleles in glucose-6-phosphate dehydrogenase that influence sensitivity to therapeutic agents, like the antimalarial drug Primaquine.

Another example of genetic variations with clinical relevance are alleles pertaining to increased risks of pathological conditions, like the Factor V Leiden allele and the increased risk of venous thrombosis. Nucleic acids isolated from bacteria can be used to detect gene coding sequences to evaluate the pathogenicity of a bacterial strain. Examples of such genes are the Lethal Factor, the Protective Antigen A, and the Edema factor genes on the PXO1 plasmid of *Bacillus anthracis* and the Capsular antigen A, B, and C on the PXO2 plasmid of the *B. anthracis*. The presence of these sequences allows researchers to distinguish between *B. anthracis* and harmless soil bacteria. Nucleic acids isolated from RNA viruses can be used to detect gene coding sequences to detect the presence or absence of a virus or to quantify a virus in order to guide therapeutic treatment of infected individuals.

A particularly significant utility of such assays is the detection of the human immunodeficiency virus (HIV), to guide anti-retroviral therapy. Nucleic acids isolated from DNA viruses can be used detect gene coding sequences to detect the presence or absence of a virus in blood prior to their use in the manufacturing of blood derived products. The detection of hepatitis B virus in pools of blood samples is a well-known example of this utility to those familiar in the art. The presence of verotoxin *Escherichia coli* in ground beef is a good example of the potential agricultural uses of the apparatus. Detecting the Norwalk virus on surfaces is an example of a public health environmental monitoring application.

EXAMPLES

The present subject matter is further illustrated by the following examples, which should not be construed as limiting in any way. The contents of all cited references (including literature references, issued patents, published patent applications as cited throughout this application) are hereby expressly incorporated by reference.

Example 1

Genotyping Panel

Multiple genotyping tests can be performed in one sample processing cartridge having a common sample preparation track and a plurality of tracks for the detection of each disease. For example, a single DNA sample can be tested for multiple genetic diseases. This may be especially useful when screening for a standard panel of genetic diseases in the general population or in a particular ethnic group in which certain diseases have increased incidence. For example, a panel for genotyping genetic diseases having increased frequency among persons of Ashkenazi Jewish descent may include tracks for one or more of Bloom syndrome, Canavan disease, Cystic fibrosis, Factor XI deficiency, Familial dysautonomia, Fanconi anemia, Gaucher disease, Mucolipidosis IV, Niemann-Pick disease, Tay-Sachs disease, and Torsion dystonia.

Figure 6:
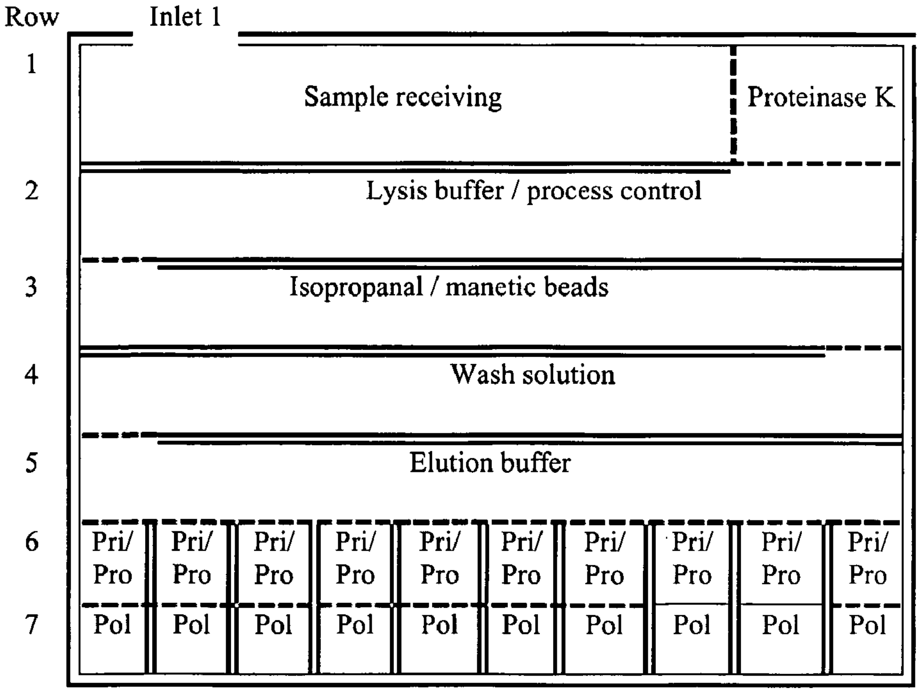
FIG. 6. is a schematic of a single input port array of segments for performing multiple nucleic acid tests using a single raw biological sample input.

A blood sample is collected and deposited into a cartridge (FIG. 6). Sample lysis, capture, wash and elution steps are performed on the sample within a plurality of segments for sample preparation and genomic DNA extraction. The detail reagents and reaction conditions used in each steps as well as the operation of the actuators in a track are detailed in U.S. patent application Ser. No. 10/773,775, hereby incorporated herein by reference. The eluted DNA is split into a plurality of tracks, and each track may contain the PCR reagents, oligonueclotide primers and probes necessary to detect one disease. A thermal cycling program is performed by alternatively moving reaction mixture between two segments set at denature temperature and annealing/extension temperature, respectively, across the plurality of tracks concurrently to amplify and detect loci for each disease. Approximately 4 alleles can be detected for each disease in a PCR track, wherein one locus is detected in a specific optical channel. Disease requiring more than 2 loci, such as cystic fibrosis, may utilize two or more tracks. The combination of multiplexing using report probes of different wavelength within a track and spatial multiplexing across multiple tracks allows the simultaneous detection of high numbers of nucleic acid targets.

Example 2

Multi-Lumen Polymerase Chain Reaction

Figure 4:
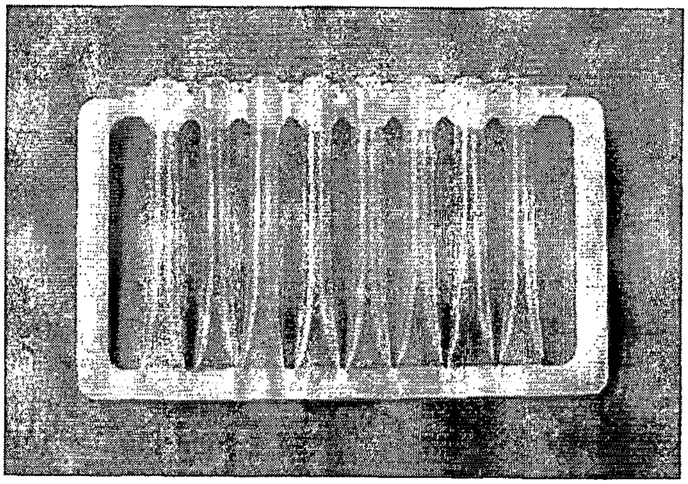
FIG. 4 is a photograph of a multi-track sample processing cartridge.

Polymerase chain reactions (PCR) on different samples can be performed in respective tracks of a cartridge. A cartridge having eight tracks (FIG. 4) with a track to track spacing similar to that of wells in a column of a 96 well plate may readily accept sample nucleic acid templates from such 96 well plates using automation fluid handling systems or manual pipetting. Similarly, a cartridge having 16 tracks with a track to track spacing similar to that of wells in a column of a 384 well plate may be used for higher throughput processing. After sample nucleic acid templates and PCR reagent mixtures are transferred into respective tracks of a sample processing cartridge, the cartridge may be placed in an analyzer which performs a thermal cycling program by alternatively moving reaction mixture between two segments set at denature temperature and annealing/extension temperature, respectively, across the plurality of tracks concurrently. The amplification reaction may be further detected in real-time.

Example 3

Air Analysis

An air analysis device and method can be used to monitor air for biological organisms and toxins through tests for the detection of specific nucleic acids (either DNA or RNA) as well as proteins. The device has an air sampler that selectively collects a population of particles into a disposable test cassette that contains all the required sample collection and reaction vessels, reagents, and reach-back sample preservations segments for one month's operation. A sample processing module within the instrument can manipulate the sample within the disposable according to programmed protocol, and a detection module within the instrument can monitor the reaction within the closed test vessel. The device contains a power source to allow for autonomous operation in the event of a power failure and a communications module to connect it to a network of similar detectors and allow for monitoring at a remote site. A control panel on the outside of the device allows for on-site diagnostics.

When operating in air collection mode, the device collects an air sample through an inlet, connected to a filter embedded in a flexible plastic membrane. The air input and air outlet flow is perpendicular to the flexible plastic membrane reaction vessel (FIG. 7). The first segment is a sample collection segment, including a filter bag to capture a population of particles. In some embodiments this filter is folded into a bag in order to increase the surface area of the filter to reduce back-pressure. In other embodiments, the filter is arranged such that one face of the filter is directed towards the inlet while the other face is orientated towards the outlet. The test segments adjacent to the filter-containing segment of the test section contain reagents, such that actuators, and clamps in the device can mix the collected sample with reagents to perform a test as well as segregate waste products from reactants. The video tape-like test cassette holds a spool of long continuous tape-like flexible test tubule, which acts as a sample vessel, and contains all the reagents required for the tests. Each test uses a new section of the disposables with pre-packed reagents to avoid cross contamination and carry-over. Normal maintenance requires only periodic (i.e., hourly, daily, weekly, monthly, bimonthly, etc.) changing of the disposable cassette.

After a set duration of air collection, the inlet and outlet adapters are retracted from the flexible plastic membrane, a heated clamp welds the input and output slits in the flexible membrane such that the segment containing the filter becomes a permanently closed reaction vessel. All of the waste generated during the sample processing methodology will remain within the test tube such that no waste is generated beyond the disposable cassette itself. A test advancing mechanism moves the flexible plastic membrane to an assay performance position within the device. When operating in sample testing mode, the device applies pressure to the flexible tape to burst peelable seals and moves liquid through the test tape. Controlling the clamp position and applying pressure to a tubule segment with an actuator results in the opening of a breakable seal and moves the pre-packed reagent to an adjacent segment. For example, the pre-packed buffers can be transferred to hydrate dry reagents stored in a test tubule segment, which can then be mixed with the particulate sample collected in the filter bag.

Fiducial features are present on the outer edge (5 mm) of the test tape that can interact with the device's mechanism to ensure proper alignment of each new test section as a new test section moves into the sample collection position and the test section that has already been used to capture a sample moves to the sample processing position. The test section is divided into many segments by peelable seals as well as permanent seals. The actuators that apply pressure to the flexible tape also control the temperature of the liquid within the tape such that moving the liquid from one segment, in contact with an actuator set at a given temperature, to another segment, in contact with another actuator set at a different temperature, will change the temperature of the fluid in the flexible tape. Reagents, such as dry antibody coated magnetic capture beads, wash buffers, spore germination/filter elution buffer, dry protein detection reagents, dry reverse transcriptase, DNA ligase & padlock probes, dry exonuclease I & exonuclease III, dry PCR reagents, dry uracil-N-glycosylase, lysis solution, dry silica coated magnetic particles, isopropanol can be pre-packed in a specified order in the segments of the test tape during the manufacturing process. The relative position of these reagents in a given linearly disposed array of segments reflects the order in which they will be used in a given sample processing method.

Placing a magnet onto an actuator can enable the device to manipulate magnetic beads within the flexible test tape. After the binding event the magnetic beads can be washed with a buffer, like phosphate buffered saline (PBS), to remove molecules that have no affinity to the capture antibodies. After the wash process, a detection reagent can be mixed with the magnetic beads. This detection reagent usually includes antibodies, however, those familiar in the art will know that a similar role can be performed by peptides, nucleic acids, virus particles or cells. Alternatively, these magnetic beads can be used as a solid phase substrate to capture specific nucleic acids when a nucleic acid is conjugated to the magnetic bead. For example, nucleic acids among total cellular lysis products generated by incubation with proteinase K, 4.7 M guanidium HCl, 10 mM Urea, 10 mM Tris.HCl pH 5.7, and 2% Triton X-100 can readily be hybridized to nucleic acids conjugated to a magnetic particle by incubation at a temperature approaching the melting point of the duplex DNA being targeted by the capture nucleic acids; e.g., 50° C. for 10 minutes. The beads can then be captured magnetically by the instrument and waste removed by successive washing with 10 mM Tris.Cl pH 7.5, 150 mM NaCl.

Nucleic acid tests are performed with padlock probes as nucleic acid intermediates between the genomic nucleic acid targets and the molecular beacon probes used to detect a sequence. Padlock probes are oligonucleotides that can form a circular complex when bound to a complementary target sequence. Circularization of padlock probes with T4 DNA ligase (Nilsson et al., 1994 Science 265: 2085-2088) or thermostable ligase (Luo et al., 1996 Nucleic Acids Res 24: 3071-78; Barany, 1991 Proc. Natl. Acad. Sci. USA 88: 89-93) can specifically and sensitively discriminate point mutations in target DNA sequences. Probes that fail to circularize or concatenate with other probes can be degraded using exonucleases to enrich circularization products 1,000 fold (Hardenbol et al., 2003 Nat Biotechnol 21: 673-8). Treatment with uracil-N-glycosylase (UNG) can then be used to eliminate all contaminant PCR products (Pang et al., 1992 Mol Cell Probes 6: 251-6) and invert the padlock probes to allow for PCR amplification of the hybridization tags each probe carries. Padlock probes can be used for the amplification of large numbers of sequences using a single set of primers, thus avoiding the difficulty of genotyping large numbers of markers using PCR (Hardenbol et al., 2003; Baner et al., 2003 Nucleic Acids Res 31: e103). Hardenbol et al., 2003 as well as Baner et al., 2003 have used this approach to score over 1,200 DNA markers in a single reaction. Padlock probes have also been used to detect RNA molecules as well as mixtures of RNA and DNA molecules using T4 DNA ligase to catalyze the probe circularization (Nilsson et al., 2000 Nat Biotechnol 18: 791-3). Chen et al. (US patent 2004/0161788 A1) have shown of such reactions can be performed in a flexible tube.

Example 4

HCV RNA and Protein Orthogonal Test

A further aspect of this disclosure is a device capable of performing tests for proteins and nucleic acids at the same time in the same reaction vessel (FIG. 1B). This disclosure offers a simple solution to this problem by splitting a raw sample, within the flexible tape, to different linearly disposed segment arrays in which the processes for nucleic acid tests and protein tests can be performed in parallel. The detection of proteins through immuno-magnetic PCR is well known to those familiar in the art. Therefore a device capable of detecting nucleic acids can also readily be used for protein detection assays.

The process through which this splitting occurs is volumetrically controlled such that each of the assays taking place in the test tape are initiated with a known volume of sample. Volumetric control is achieved by compressing the test tape over a segment containing a liquid sample 112, while simultaneously raising the actuators compressing adjacent segments 21 22 to a volume matching the desired volume. This process is conducted in a device (FIG. 1B), including at least a two-row by two-column array of segments, each of which is defined by the walls of the sample vessel. These segments are fluidly isolated at least in part by a breakable seal 41 42 74 and by at least one permanent seal 71 which defines the two sample processing paths. The reaction vessel is so expandable as to receive a volume of fluid expelled from another segment and so compressible as to contain substantially no fluid when so compressed. The segments are aligned such that substantially all the segments in a row are capable of being compressed simultaneously by the sample processing device applying pressure to the vessel. A clamp, situated between two actuators can then close the fluid contact between the segment which delivered the fluid sample and the two segments which received the liquid sample.

In a preferred embodiment, a cartridge with one input port is used to input a raw sample which is volumetrically split between two linearly disposed contiguous segments separated by peelable seals and containing reagents to perform tests on two different types of analytes, from a common microbial agent such as HIV or HCV, within a single clinical sample. As this embodiment measures the quantity of coat protein and the quantity of RNA genome in a plurality of virions in a given clinical sample, the relative proportions of each portion of the split sample will depend on the relative affinity of the immunological reagents used to detect the protein and the sensitivity of the immuno-PCR assay relative to the sensitivity of the RT-PCR assay used to detect the RNA genome. The volume of the input sample will also depend on the sensitivity of these assays as well as the titer of the virus in a given human clinical sample.

Figure 8:
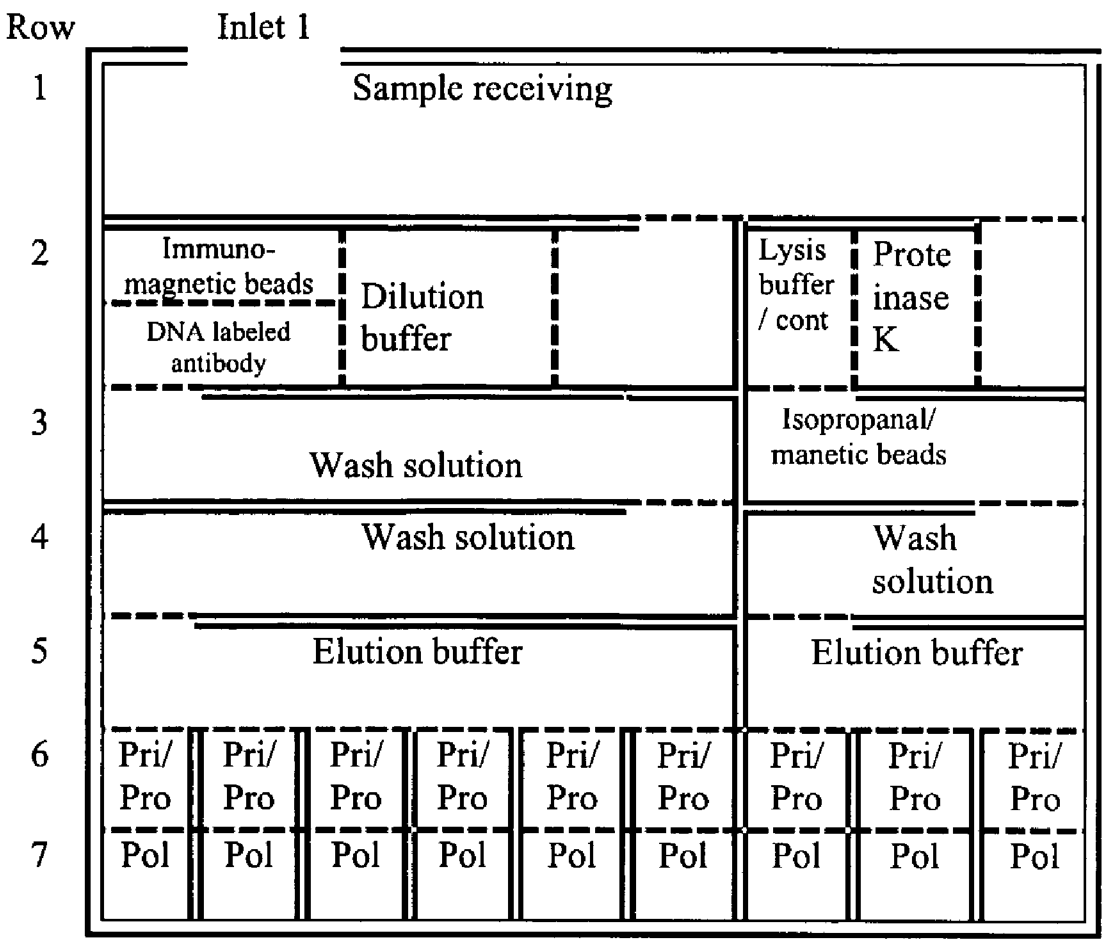
FIG. 8 is a schematic of a single input port array of segments for performing nucleic acid and protein tests on a single sample in which said sample is volumetrically split between the two paths.

For HCV detection, the sample input will be blood and the volume will be ~100 μL. This embodiment uses a cartridge (FIG. 8) which contains multiple segments defined by peelable seals which create temporary barriers to liquid movement both in the horizontal and vertical direction. When pressure is applied to the peelable seals by actuators, these open permanently. Clamps, similar to actuators but with a narrow edge, are used to break fluid contacts. The first segment adjacent to the sample input port, receives the sample. The cartridge contains two sample processing paths: a protein assay path and a DNA assay path. These paths are separated by a permanent seal. The segment adjacent to the sample input chamber in the DNA path is divided in two by a peelable seal: one portion contains a proteinase K pellet while the other holds lysis buffer, a chaotropic salt-based cell buffer that releases DNA from cells.

In contrast, the segment adjacent to the sample input chamber in the protein path is also divided in two: one portion contains immuno-magnetic beads, a reagent that will specifically bind a protein analyte targeted by the assay, while the other portion contains a dilution buffer which redisolves the immuno-magnetic reagent and mixes it in with the sample. In the DNA assay path, segment adjacent to the proteinase K/lysis buffer segment contains isopropanol and MagPrep beads, such that nucleic acids are precipitated onto the magnetic particles in that segment when the peelable seal is broken to mix the contents of the two segments. The magnetic beads are then successively washed by buffer released from segments containing wash buffer in order to remove PCR inhibitors. In the protein assay path, the immobilized immuno-magnetic particles mixed with detection reagents, stored in segment, and then washed with a different buffer solution, released from two contiguous segments. After these washes, the magnetic beads are heated with PCR elution buffer prior to being immobilized. The solution, which contains the analyte nucleic acids, as well as the reporter nucleic acids for the immuno-PCR assays, are transferred to a segment containing primer/probe, while the magnetic beads are retained in the segments. The analyte probes and primers are then transferred to a segment containing DNA amplification enzyme.

Example 5

HIV RNA Quantitation and CD4+ Cell Counts

A further embodiment of this disclosure is the use a cellular assays and molecular diagnostics in clinical patient management. The treatment of patients infected with HIV uses combinations of anti-retroviral drugs (a.k.a. highly active anti-retroviral therapy of HAART). As the genome of HIV mutates rapidly, virus populations in patients receiving anti-retroviral drugs are subjected to selective pressure in favor of drug resistant strains. Treating physicians typically monitor the patient's immune system (i.e., CD4+ count) as well as the copy number of the HIV virion in the patient's blood as a means of detecting the emergence of resistant strains of the virus and pending HAART therapeutic failure (Hughes 1997, Ann Intern Med 126:929-38: Mellors 1997 Ann Intern Med 126:946-54; O'Brien (1997) Ann Intern Med 126:939-45). A drop in the CD4+ cell count is also typically seen in many other diseases, such that a diagnosis of AIDS must include evidence of the HIV virion or antibodies to the virion. As the typical count variation (from 50-150 cells/μl in HIV patients vs. non-HIV patients: 800-1200 cells/μl), a large enough volume of blood is required to get an accurate cell count.

The two input port device described in this disclosure can be used to perform a CD4+ cell count as well as an HIV RNA quantitation. In this embodiment, a cellular assay is performed by mixing a 5 μl blood sample with 500 μl of a dilution buffer (the blood also needs to be diluted 100-fold to allow individual cells to be imaged) stored in the second segment relative to the input port as well as with a fluorescent antibody that selectively binds to the CD4+, stored in a portion of the first segment which received the blood sample. The stained cells are then flowed though a compressed section of the cartridge located in the third segment. As the cells pass through this thin flow sheet, the fluorescent cells are detected by a CCD camera in the diagnostic device.

The segment adjacent to the second input port receives a large volume of blood (2 mL in order to accurately measure the quantity of HIV RNA). The subsequent segments of this RNA path may include the lysis solution, magnetic particles conjugated to oligonucleotides with homology to HIV RNA, wash buffer, elution buffer, dry RT-PCR reagents (i.e., reverse transcriptase, PCR primers, DNA polymerase, and dual-labeled probe). Nucleic acids among total cellular lysis products generated by incubation with proteinase K, 4.7 M guanidium HCl, 10 mM Urea, 10 mM Tris HCl pH 5.7, and 2% Triton X-100 can readily be hybridized to nucleic acids conjugated to a magnetic particle by incubation at a temperature approaching the melting point of the duplex DNA being targeted by the capture nucleic acids; e.g., 50° C. for 10 minutes. The beads can then be captured magnetically by the instrument and waste removed by successive washing with 10 mM Tris.Cl pH 7.5, 150 mM NaCl, prior to elution and PCR analysis.

Example 6

Her2 DNA, RNA and Protein Test

HER2 is recognized as an important predictive and prognostic factor in breast cancer (Slamon, et al. 1987 Science 235:177-182). HER2 gene amplification is a permanent genetic change that results in the continuous overexpression of the HER2 receptor (HER2 protein) (Kallioniemi 1992. Proc Natl Acad Sci USA. 89:5321-5325). Several studies have shown that HER2 overexpression (either extra copies of the gene itself, or an excess amount of the gene's protein product) is associated with decreased overall survival. Patients with HER2 overexpression are receptive to treatment with Herceptin (Genentech).

There are two FDA-approved tests to determine HER2 status and select patients for treatment with Herceptin. The first approved was an immunohistochemistry test (DAKO, HercepTest®), which measures the level of expression of the HER2 protein on cell surfaces. The second is fluorescence in situ hybridization (FISH) measurement (Vysis, PathVysion®) to measure the number of HER2/neu gene copies. In HER2-positive tumors, there are 2 or more copies of the HER2/neu gene per chromosome 17 due to gene amplification of HER2/neu. Those familiar in the art will know that gene copy number can also be detected by real time PCR (Suo et al. 2004 Int J Surg Pathol. 12:311-8). A third test, the Bayer Immuno 1® HER2/neu serum test, is approved only for use in the follow-up and monitoring of patients with metastatic breast cancer. The test measures circulating levels of the shed extracellular domain of HER2 (ECD-Her2), but does not measure either gene amplification or overexpression of HER2 on the surface of tumor cells. In normal individuals the level of HER2-ECD is less than 15 ng/mL while in HER2-positive patients it may be several times higher.

Overexpression of HER2 protein rarely occurs in the absence of gene amplification. FISH analysis reveals that some patients with apparent protein overexpression (IHC 2+ or 3+) do not have gene amplification (FISH-), suggesting that these patients may be "false positives" (Press et al. 1994 Cancer Res. 54:2771-2777). Approximately 2%-4% of patients who demonstrated HER2 protein overexpression by molecular techniques do not have gene amplification (Lohrisch et al. 2001, Clin Breast Cancer 2:129-135). In current laboratory testing, variability in pre-analytical tissue processing, reagent variability, antigen retrieval, and scoring may result in immunohistochemistry false-positives. Those familiar in the art will know that a test for Her-2 RNA could provide complementary information to the protein test or the DNA copy number test and thus help reduce the "false positive" by detecting gene expression, which could detect increased expression even if the immunohistochemistry assay fails and/or the patients tissue lacks gene amplification.

A preferred embodiment of this disclosure is a device that can quantify serum ECD-HER2 using a serum input, as well as detect DNA copy number and RNA copy number of the Her-2 gene using a second input of tissue from a biopsy. The amount of serum input into a first port ranges from 10 μL to 100 μL while the biopsy input in a second port is from a needle biopsy. The serum is diluted with a buffer stored in the second compartment and the Her2-ECD is captured by antibodies conjugated to magnetic beads, also stored as a dry reagent in the second segment but separated from the dilution buffer by a peelable seal. After an incubation, the ECD-HER2 is captured by the magnetic beads, and washed with buffer released from segments adjacent to the second segment. After the wash, the magnetic beads are heated with PCR elution buffer prior to being immobilized. The solution, which contains the analyte nucleic acids, as well as the reporter nucleic acids for the immuno-PCR assays, are transferred to a segment containing primer/probe, while the magnetic beads are retained in the segments. The analyte probes and primers are then transferred to a segment containing DNA amplification enzyme.

In contrast, the tissue biopsy input into the other port is digested by incubation with proteinase K, 2.4 M guanidium HCl, 5 mM Urea, 5 mM Tris HCl pH 5.7, and 1% Triton X-100. The subsequent segments of this RNA/DNA path may include silica coated magnetic particles in isopropanol, such that nucleic acids are precipitated onto the magnetic particles in that segment when the peelable seal is broken to mix the contents of the two segments. The magnetic beads are then successively washed by buffer released from segments containing wash buffer in order to remove reverse transcription and PCR inhibitors. The sample is then split in two using the approach as previously described to perform an RT-PCR and PCR amplification in parallel tacks.

Example 7

Detection of Protein Toxin and Bacterial DNA in a Sample

Figure 5:
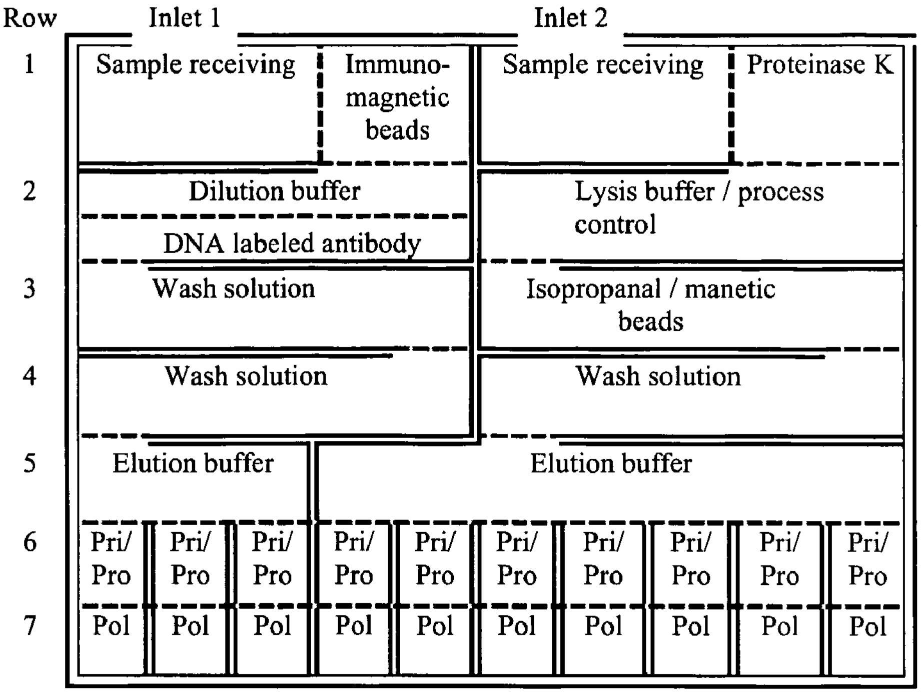
FIG. 5 is a schematic of a two port sample processing cartridge for performing immuno-PCR tests for proteins and PCR test for nucleic acid.

In another embodiment, a sample processing cartridge (FIG. 5) with two input ports is used to detect bacterial toxins and bacteria in a food sample. In a preferred embodiment, a cartridge with two input ports is loaded with liquid samples that have undergone filtration to selectively capture bacteria and proteins that may be present in a clinical or a food sample. For example, such a system is capable of performing assays for one agent by detecting both the toxin produced by a bacterium, such as *Bacillus anthracis*, as well as detecting the nucleic acid genome or RNA produced by the bacterium itself. Alternatively, such a system may perform concurrent assays for multiple toxins, such as staphylococcal enterotoxin and *Clostridium botulinum* neurotoxin, and bacteria, such as *E. coli* and *Salmonella* spp. The filtered sample containing filtered bacterial cells is transferred to one input port while that containing free proteins is placed into the other port. The cartridge contains multiple segments defined by peelable seals which create temporary barriers to liquid movement. When pressure is applied to the peelable seals by actuators, these open permanently. The sample receiving segments adjacent to the sample input ports receives the sample. The cartridge contains two sample processing tracks: a protein assay track and a DNA assay track. The array of segments and the reagent contained in the segments are shown in FIG. 5.

In the DNA track, a sample is introduced into the sample receiving segment. After the interceding breakable seal is burst, the sample mixes with and reconstitutes the proteinase K pellet. The solution is then transferred to the next segment, and mixed with a chaotropic salt-based cell lysis buffer to release DNA from cell lysates. After lysis, the sample solution is transferred to an adjacent segment containing isopropanol and silica magnetic beads (e.g. MagPrep® Silica, Merck & Co.) to precipitate nucleic acids onto the bead surface. The DNA bound beads are then captured magnetically to retain the beads in the segment, while wash buffer from the next segment is used to wash the beads and remove potential PCR inhibitors. Thereafter, the beads are magnetically released, and elution buffer is transferred to release the DNA from the bead surface. The eluted DNA solution is then transferred and split into the PCR sub-tracks, mixed with primers (Pri) and probes (Pro), and PCR reagents including DNA polymerase (Pol), and a thermal cycling program is performed to amplify and detect the DNA in real-time.

In the protein track, a sample deposited into the sample receiving segment is mixed with immuno-magnetic bead, during which the protein analytes targeted by the assay is specifically bound. The solution is then transferred to the next segment and mixed with dilution buffer and DNA labeled antibodies specific for the protein analytes. Complexes formed by the protein analyte, immuno-magnetic bead and DNA labeled antibody is captured magnetically, and washed twice using the wash buffer from the next two segments. After washing, the bead complexes are magnetically released and the elution is transferred and mixed with the beads to elute DNA labels. The eluted DNA solution is then transferred to the PCR sub-tracks for amplification and real-time detection.

We claim:

1. A method of processing sample, comprising:

introducing at least one sample into at least one segment of a plurality of segments arranged in an array at least two rows long and two columns wide, each segment of the array being:

fluidly isolated from adjacent segments at least in part by at least one breakable seal or by at least one permanent seal;

so expandable as to receive a volume of fluid expelled from another segment; and so compressible as to contain substantially no fluid when so compressed;

wherein at least two adjacent segments in at least one row are separated by a permanent seal to form at least two tracks; and wherein at least one segment is a branch segment either in fluid communication with the at least two tracks or isolated from the two tracks by one or more breakable seals;

incubating the sample in a segment with a substance capable of specific binding to a preselected component of the sample;

moving a fluid from a first segment to an adjacent second segment by compressing the first segment and propelling the fluid into the second segment; and splitting a fluid from a branch segment into the at least two tracks, wherein splitting comprises:

compressing a receiving segment of each track;

decompressing each receiving segment to define a gap to control the volume of the segment;

compressing the branch segment to fill receiving segments of each track with a defined volume; and fluidly isolating the receiving segment of each track from the branch segment.

2. A method of processing sample, comprising:

introducing at least one sample into at least one segment of a plurality of segments arranged in an array at least two rows long and two columns wide, each segment of the array being:

fluidly isolated from adjacent segments at least in part by at least one breakable seal or by at least one permanent seal;

so expandable as to receive a volume of fluid expelled from another segment; and so compressible as to contain substantially no fluid when so compressed;

wherein at least two adjacent segments in at least one row are separated by a permanent seal to form at least two tracks; and wherein at least one segment is a branch segment either in fluid communication with the at least two tracks or isolated from the two tracks by one or more breakable seals;

filtering a sample through a filter segment comprising a filter dividing the segment into section A and section B, wherein section A connects to at least one track through a breakable seal, and section B connects to an upstream segment containing wash fluid through a breakable seal, section A further comprising an inlet and section B further comprising an outlet, by:

urging a fluid from the input through the filter from section A to section B to the output;

closing the input and output;

compressing the upstream segment containing wash fluid, thereby opening a breakable seal and propelling a wash fluid into section B through the filter and into section A;

clamping between the upstream segment and filter segment; and compressing filter segment, thereby opening a breakable seal and propelling fluid from the filter segment to at least one track;

incubating the sample in a segment with a substance capable of specific binding to a preselected component of the sample;

moving a fluid from a first segment to an adjacent second segment by compressing the first segment and propelling the fluid into the second segment;

and splitting a fluid from a branch segment into the at least two tracks.

3. The method of claim 1 or claim 2, wherein the volume split into a receiving segment of a first track differs from the volume split into the receiving segment of a second track, wherein the volume split into each receiving segment is defined by a width of the respective receiving segment.

4. The method of claim 1 or claim 2, further comprising merging fluids from the at least two tracks into a branch segment connected to the at least two tracks through breakable seals by compressing at least one segment of each of the at least two tracks.

5. The method of claim 1 or claim 2, further comprising processing fluids in the at least two tracks by concurrently compressing at least one segment of each of the at least two tracks in the same row of the array of segments.

6. The method of claim 1 or claim 2, further comprising at least one of moving a fluid from one track to another track, capturing the substance, releasing a reagent, reconstituting a dry reagent, forming a thin-layer flow channel, mixing a quantity of fluid, agitating a quantity of fluid, urging the sample through a filter, grinding the sample, adjusting the volume of a fluid, removing an air bubble, eluting the sample, lysing a sample and removing waste from the preselected component.

7. The method of claim 1 or claim 2, wherein the preselected component comprises a nucleic acid, and the method further comprises amplifying the nucleic acid by at least one of polymerase chain reaction, reverse transcription polymerase chain reaction, rolling circle amplification, ligase chain reaction, nucleic acid based amplification, transcription mediated amplification, and strand displacement amplification reaction.

8. The method of claim 1 or claim 2, further comprising performing a first assay in a first track and a second assay in a second track, wherein the first assay and second assay each are of a type selected from the group consisting of deoxyribonucleic acid assay, ribonucleic acid assay, protein assay, immunoassay, and cellular assay.

9. The method of claim 1, further comprising filtering a sample through a filter segment comprising a filter dividing the segment into section A and section B, wherein section A connects to at least one track through a breakable seal, and section B connects to upstream segment containing wash fluid through a breakable seal, section A further comprising an inlet and section B further comprising a outlet, by:

urging a fluid from the input through the filter from section A to section B to the output;

closing the input and output;

compressing upstream segment containing wash fluid, thereby opening a breakable seal and propelling a wash fluid into section B through the filter and into section A;

clamping between the upstream segment and filter segment; and compressing filter segment, thereby opening a breakable seal and propelling fluid from the filter segment to at least one track.

10. The method of claim 8, wherein the first assay is of a type different from that of the second assay.

11. The method of claim 8, wherein the first assay is a deoxyribonucleic acid assay or a ribonucleic acid assay, and the second assay is a protein assay or an immunoassay.

12. The method of claim 8, wherein the first assay is a deoxyribonucleic acid assay or a ribonucleic acid assay, and the second assay is cellular assay.

13. The method of claim 8, wherein the first assay is a protein assay or an immunoassay, and the second assay is cellular assay.

14. The method of claim 8, wherein processing steps in the first assay are different from processing steps in the second assay.

15. The method of claim 8, wherein:

volumes of fluid are moved from segment to segment in the array by compressing segments with actuators; and multiple actuators are positioned along a row, cross different tracks in the row, and compress segments in the different tracks independently of one another.

* * * * *